United States Patent
Yoo et al.

(10) Patent No.: US 11,083,910 B2
(45) Date of Patent: Aug. 10, 2021

(54) PET CARE DEVICE AND METHOD FOR CONTROLLING PET CARE DEVICE

(71) Applicant: LG ELECTRONICS INC., Seoul (KR)

(72) Inventors: Hyunsun Yoo, Seoul (KR); Miju Kim, Seoul (KR); Hyewon Kim, Seoul (KR); Ilha Park, Seoul (KR); Wookjun Chung, Seoul (KR); Jaehung Chun, Seoul (KR); Yousook Eun, Seoul (KR); Joogyeom Kim, Seoul (KR); Sungkyung Kim, Seoul (KR); Myongsun Kim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 16/574,302

(22) Filed: Sep. 18, 2019

(65) Prior Publication Data

US 2020/0086137 A1    Mar. 19, 2020

Related U.S. Application Data

(60) Provisional application No. 62/733,242, filed on Sep. 19, 2018.

(30) Foreign Application Priority Data

Feb. 15, 2019    (KR) .......................... 10-2019-0018025

(51) Int. Cl.
    *A61N 5/06*    (2006.01)

(52) U.S. Cl.
    CPC ......... *A61N 5/0617* (2013.01); *A61N 5/0624* (2013.01); *A61N 2005/063* (2013.01);
    (Continued)

(58) Field of Classification Search
    CPC .......... A61N 5/0617; A61N 2005/0629; A61N 2005/0652; A61N 2005/063;
    (Continued)

(56) References Cited

U.S. PATENT DOCUMENTS

| | | | |
|---|---|---|---|
| 2007/0185553 A1* | 8/2007 | Kennedy | A61N 5/0616 607/100 |
| 2010/0104471 A1 | 4/2010 | Harmon et al. | |

(Continued)

FOREIGN PATENT DOCUMENTS

| | | |
|---|---|---|
| CN | 103491924 | 1/2014 |
| CN | 107048665 | 8/2017 |

(Continued)

OTHER PUBLICATIONS

European Search report dated Dec. 16, 2019.
(Continued)

*Primary Examiner* — Carl H Layno
*Assistant Examiner* — Aya Ziad Bakkar
(74) *Attorney, Agent, or Firm* — Ked & Associates LLP

(57) ABSTRACT

A pet care device may include a removable or swappable care tool mounted on a head. The head may include a sterilizer and a sensor to determine what kind of care tool is mounted. A controller may identify the type of care tool mounted on the head based on a sensing value of the sensor and control the sterilizer based on the identified care tool.

20 Claims, 15 Drawing Sheets

(52) U.S. Cl.
CPC ............... *A61N 2005/0629* (2013.01); *A61N 2005/0644* (2013.01); *A61N 2005/0652* (2013.01); *A61N 2005/0661* (2013.01)

(58) Field of Classification Search
CPC .. A61N 2005/0644; A61B 90/90; A61B 7/04; A01K 13/002
See application file for complete search history.

(56) References Cited

U.S. PATENT DOCUMENTS

| | | | |
|---|---|---|---|
| 2011/0308034 | A1 | 12/2011 | Powers et al. |
| 2013/0197495 | A1* | 8/2013 | Koifman et al. ...... A61B 18/20 606/17 |
| 2015/0305969 | A1 | 10/2015 | Giraud et al. |
| 2017/0372634 | A1 | 12/2017 | Straka et al. |
| 2018/0161951 | A1* | 6/2018 | Billings et al. ......... B25F 5/021 |

FOREIGN PATENT DOCUMENTS

| | | |
|---|---|---|
| CN | 107343697 | 11/2017 |
| CN | 107646725 | 2/2018 |
| KR | 10-2005-0076471 | 7/2005 |
| KR | 10-2006-0007303 | 1/2006 |
| KR | 10-2006-0116425 | 11/2006 |
| KR | 20-2009-0007699 | 7/2009 |
| KR | 10-2013-0116994 | 10/2013 |
| KR | 20-2016-0002747 | 8/2016 |
| KR | 10-2017-0119434 | 10/2017 |
| KR | 10-1816704 | 1/2018 |
| WO | WO 2018/013581 | 1/2018 |

OTHER PUBLICATIONS

European Search Report dated Feb. 18, 2020 issued in Application No. 19197714.9.
U.S. Appl. No. 16/572,851, filed Sep. 17, 2019.
U.S. Appl. No. 16/574,362, filed Sep. 18, 2019.
European Search Report dated Feb. 19, 2020 issued in Application No. 19198169.5.
Chinese Office Action dated May 7, 2021 issued in CN Application No. 201910884786.0.
Chinese Office Action issued in Application No. 201910886990.6 dated Apr. 21, 2021.

* cited by examiner

FIG. 5
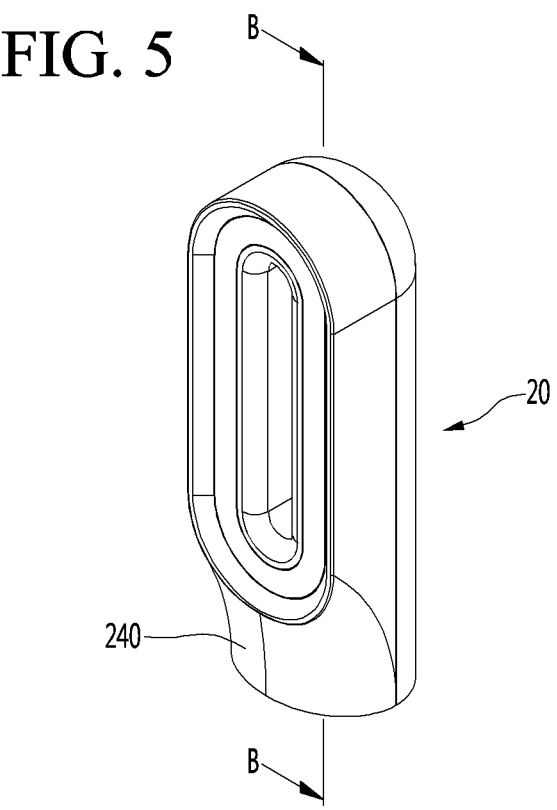
FIG. 6
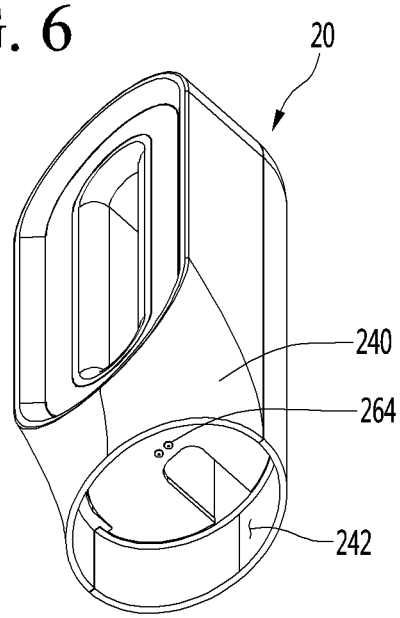
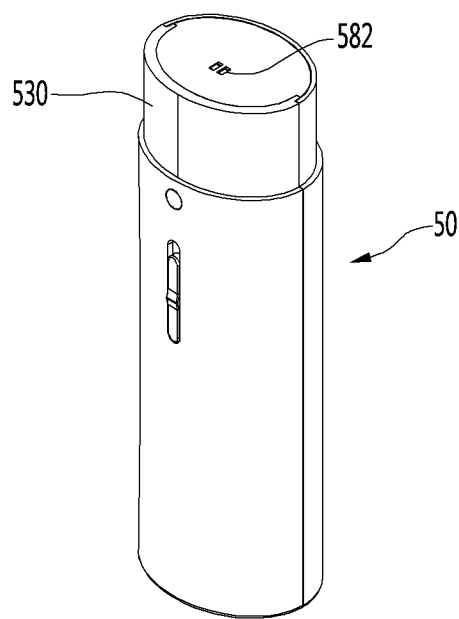
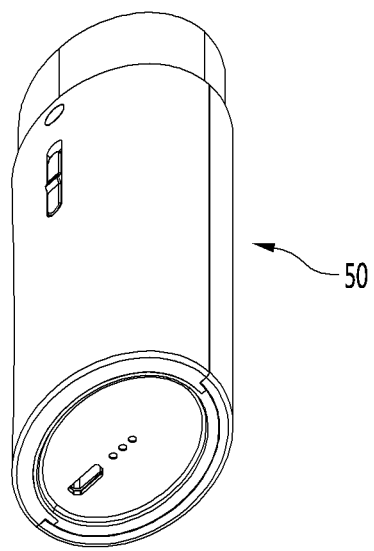

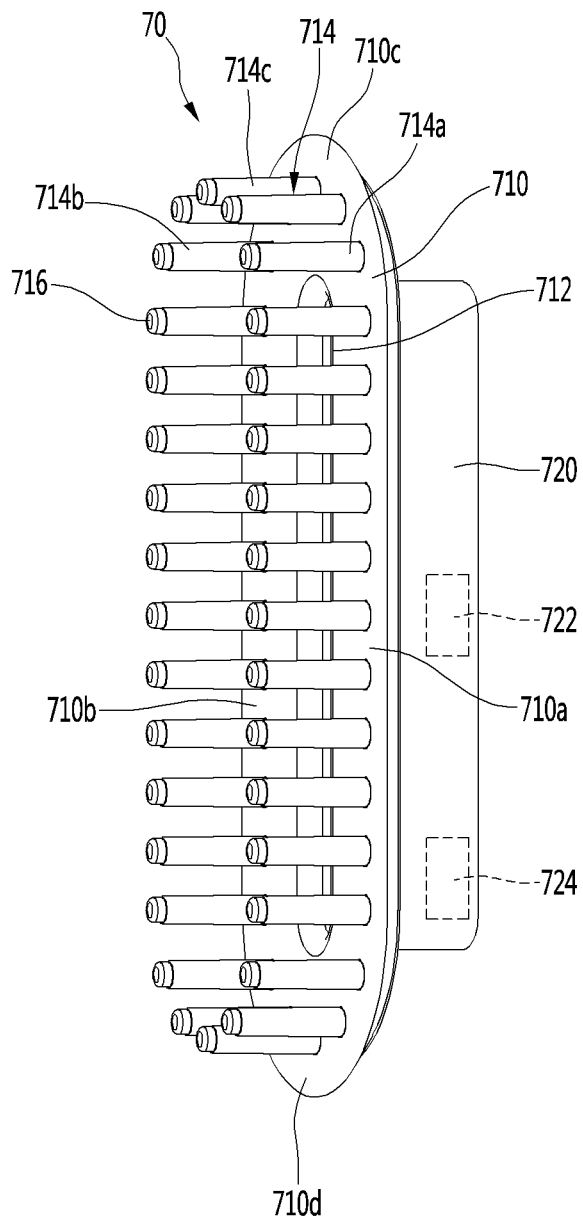
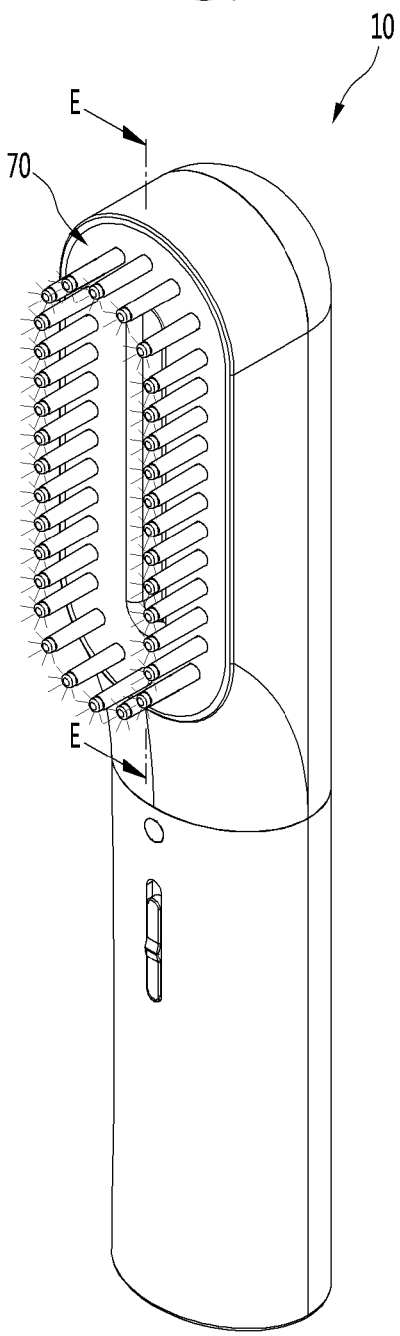

FIG. 14
FIG. 15
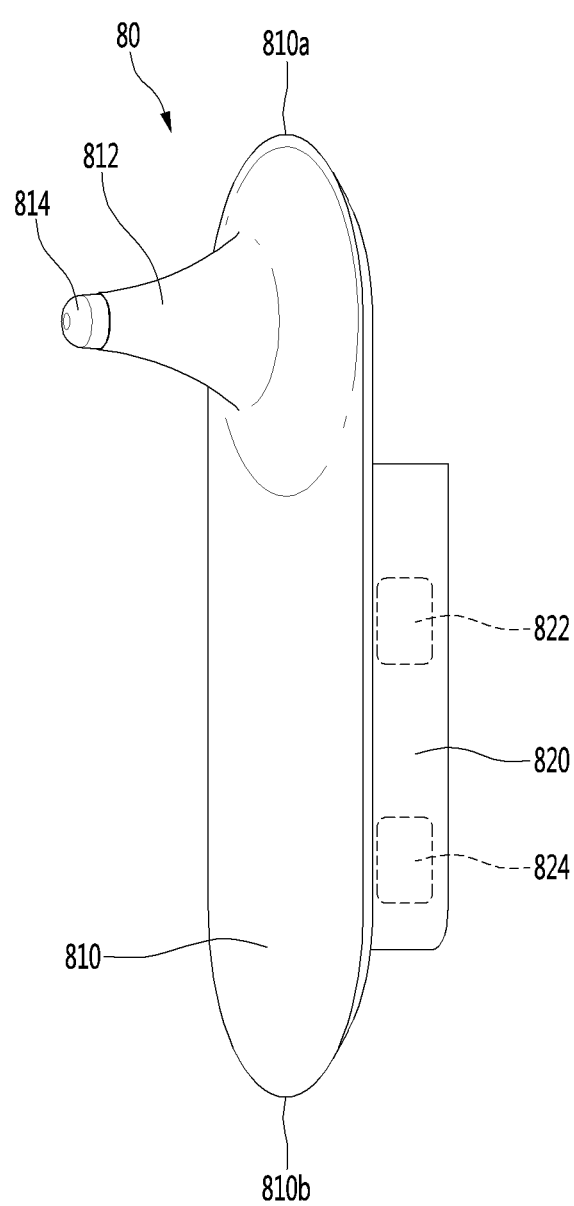
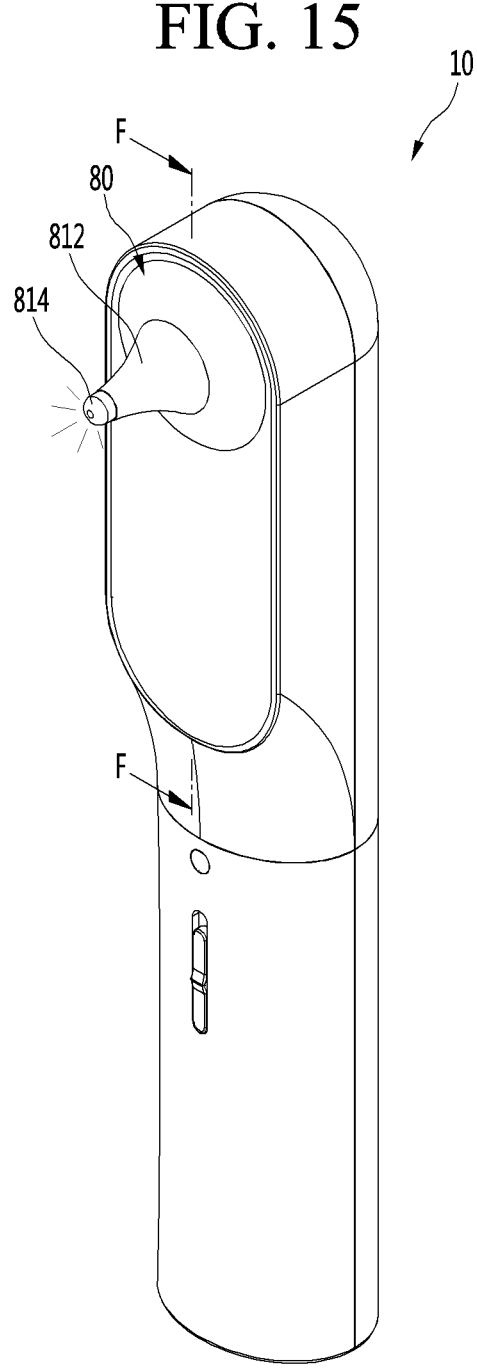

PET CARE DEVICE AND METHOD FOR CONTROLLING PET CARE DEVICE

CROSS-REFERENCE TO RELATED APPLICATION(S)

This application claims priority under 35 U.S.C. § 119 to U.S. Provisional Application No. 62/733,242 filed Sep. 19, 2018 and Korean Application No. 10-2019-0018025 filed on Feb. 15, 2019, whose entire disclosure(s) is/are hereby incorporated by reference.

BACKGROUND

1. Field

The present disclosure relates to a pet care device and a control method of a pet care device.

2. Background

In recent years, the population of people raising pets has increased, to attachment and interest in pets. As a result, pet care devices to manage and treat pets are being developed. Skin care and hair care of a pet are particularly important. If neglected, pet hair may become matted and moisture may increase, creating an environment where a variety of parasites and bacteria may live. As various diseases occur on the skin of the pet or as a pet's health condition worsens, cost and effort in treating the pet may increase.

Korean Patent Publication No. 10-2005-0076471 discloses a pet care devices. However, such a pet care device may have various disadvantages, which the present disclosure solves.

The above references are incorporated by reference herein where appropriate for appropriate teachings of additional or alternative details, features and/or technical background.

BRIEF DESCRIPTION OF THE DRAWINGS

The embodiments will be described in detail with reference to the following drawings in which like reference numerals refer to like elements wherein:

FIGS. 5 and 6 are views showing a state in which the head and the handle constituting the main body are separated from each other;

FIG. 11 is a perspective view of a first care tool;

FIG. 12 is a perspective view illustrating a state in which a first care tool is coupled to a main body;

FIG. 14 is a perspective view of a second care tool;

FIG. 15 is a perspective view illustrating a state in which the second care tool is coupled to a main body;

DETAILED DESCRIPTION OF THE INVENTION

Figure 1:
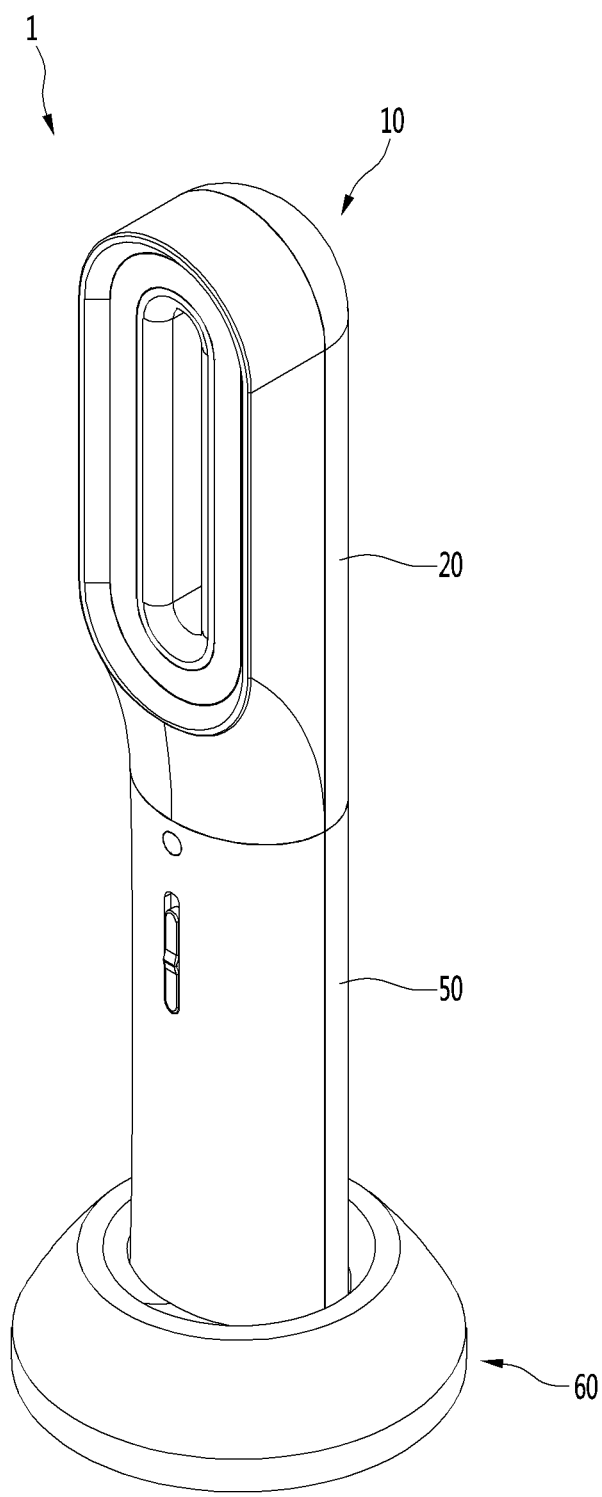
FIG. 1 is a view showing a pet care device according to an embodiment.
Figure 2:
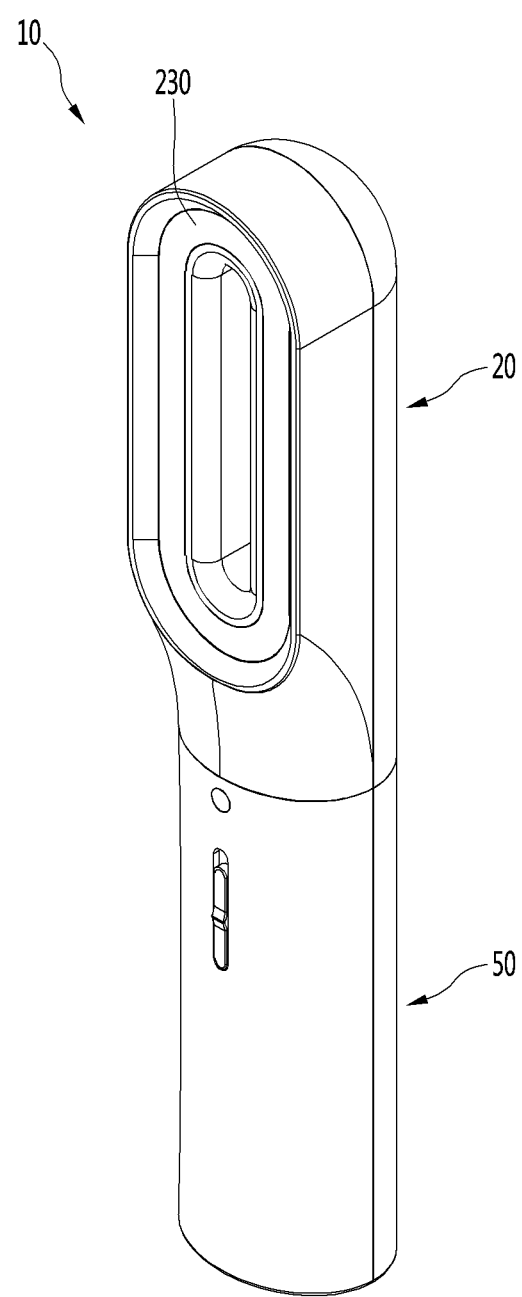
FIG. 2 is a perspective view of a main body according to an embodiment.
Figure 3:
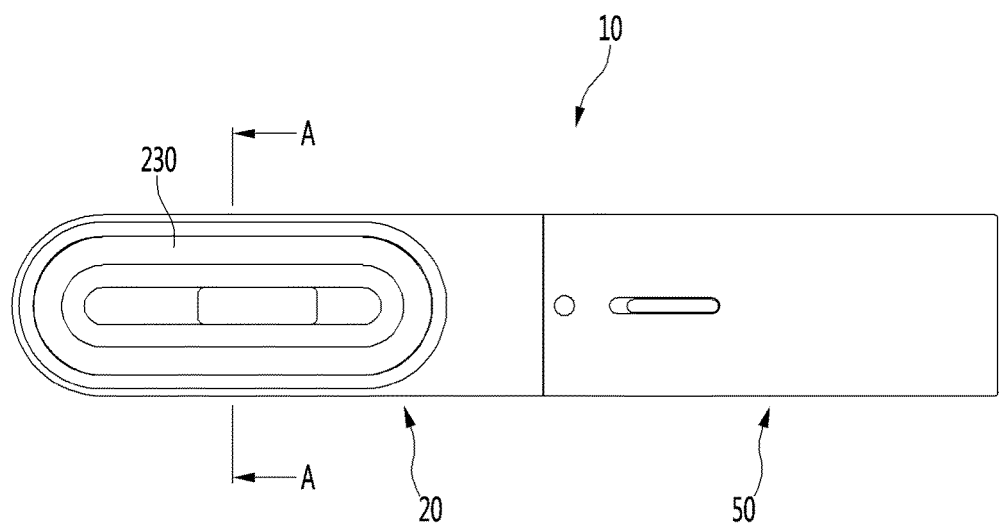
FIG. 3 is a plan view of the main body of FIG. 2.

Referring to FIGS. 1 to 3, a pet care device 1 may include a main body 10 for managing pet skin or hair. The main body 10 may include a handle 50 that a user may hold a head 20 connected to the handle 50. The user may manage the skin or hair of a pet by holding the handle 50 to aim the head 20 toward the pet. The head 20 and the handle 50 may extend in a longitudinal direction.

The head 20 may include a sterilizer 220 (FIG. 7) to be described later, and the handle 50 may supply power to the sterilizer 220. The head 20 may include a light diffuser 230 through which light emitted from a light emitting device 223 provided in the sterilizer 220 and behind the light diffuser 230 is transmitted. Light may be irradiated through the light diffuser 230 of the head 20. The skin of the pet may be managed by using light emitted through the light diffuser 230.

The sterilizer 220 may include at least one light emitting device 223. The light emitting device 223 may be an ultraviolet light emitting diode (UV LED). The UV LED may irradiate light in an ultraviolet wavelength region (e.g., UV-C region). Since the ultraviolet light irradiated by the UV LED may not be visually recognized by the user, at least one light emitting device 223 may be a red LED which emits red light together when the light emitting device 223 that emits ultraviolet light. The user may be informed that the sterilizer 220 is on via the red LED of the light emitting devices 223. When ultraviolet light is irradiated toward pet skin, bacteria or viruses may be removed, skin diseases may be treated, and skin health may be maintained.

The light diffuser 230 may be provided in a predetermined area of the head 20. Light may be transmitted only at a portion of the head 20 where the light diffuser 230 is provided. The user may manage pet skin by bringing the light diffuser 230 toward an area that needs management or treatment. Light of the sterilizer 220 may be prevented from being unnecessarily irradiated to an area outside the skin of the pet.

The pet care device 1 may further include a base or support 60 to support the main body 10. A lower end of the handle 50 may be seated on the base 60 so that the main body 10 may be erect upright. When the main body 10 is seated on the base 60, the battery 540 in the handle 50 may be charged.

Figure 4:
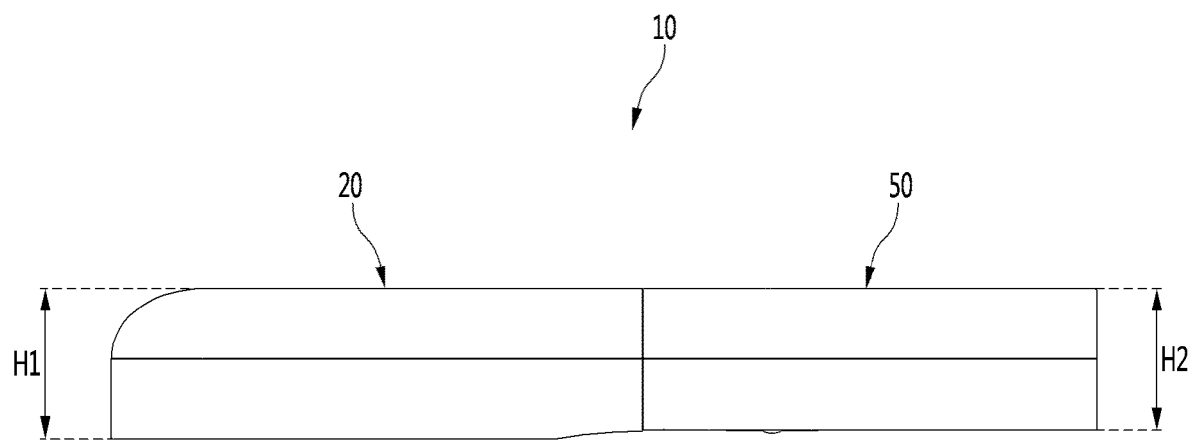
FIG. 4 is a side view of the main body of FIG. 2.

Referring to FIG. 4, a height H1 of the head 20 may be formed to be higher than a height H2 of the handle 50. The skin or hair of the pet may be prevented from being in unnecessary contact with the handle 50 during use. The user may grip the handle 50 to move the head 20 along the pet skin or hair, and a height difference between the height H1 of the head 20 and the height H2 of the handle 50 may minimize fatigue to a user's wrist. The head 20 may be configured to be detachable from the handle 50, or alternatively may be integrally formed with the handle 50 or permanently fixed to the 50.

FIGS. 5 and 6 show an example where the head 20 is detachable from the handle 50. When the head 20 is separated from the handle 50, the head 20 may be easily cleaned. There is an advantage in that the head 20 may be washed with a liquid (e.g., water) when a battery 540 that powers the head 20 (FIG. 7) is provided in the handle 50, and there is not a battery in the head 20. In such a case, the handle 50 should not contact water. Since the light emitting device 223 may be included in the head 20, the head 20 and/or light diffuser 230 be waterproofed so water does not contact the light emitting device 223 during washing.

The head 20 may include a first coupler 240 that couples to a second coupler 530 of the handle 50. A coupling between the first coupler 240 and the second coupler 530 are not limited. As an example where the head 20 is detachable coupled to the handle 50, the first and second couplers 240 and 530 may be insertably coupled.

For example, the second coupler 530 may be inserted into a coupling space 242 of the first coupler 240 along the longitudinal direction of the main body 10. The second coupler 530 may be formed as a recessed portion of the handle 50 such that an outer diameter of the second coupler 530 is less than an outer diameter of the rest of the handle 50. A size and shape of the coupling space 242 of the first coupler 240 may be configured to correspond to a shape or outer contour of the second coupler 530.

To prevent the first coupler 240 and the second coupler 530 from being separated from each other in a coupled state, each of the first coupler 240 and the second coupler 530 may include magnets or a metal so that the head 20 and the handle 50 are further coupled via magnetic attraction. For example, a first magnet having a first pole or polarity may be provided at the first coupler 245, and a second magnet having a second pole or polarity opposite to the first pole or polarity is provided at the second coupler 530. Alternatively, the first coupler 240 may be provided with a magnet, and the second coupler 530 may be provided with a metal (e.g., ferromagnetic or paramagnetic metal).

Figure 7:
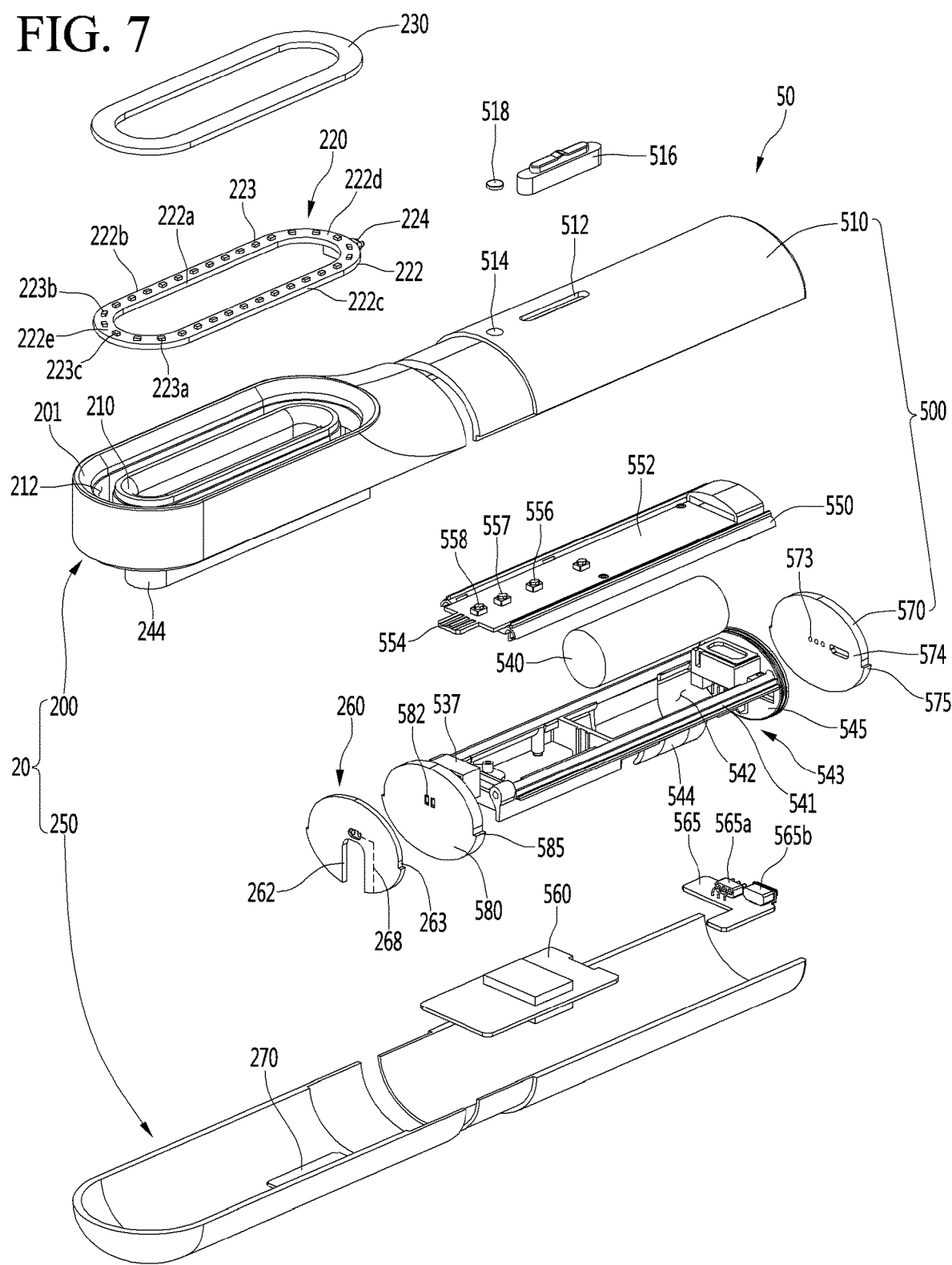
FIG. 7 is an exploded perspective view of a main body according to an embodiment.
Figure 8:
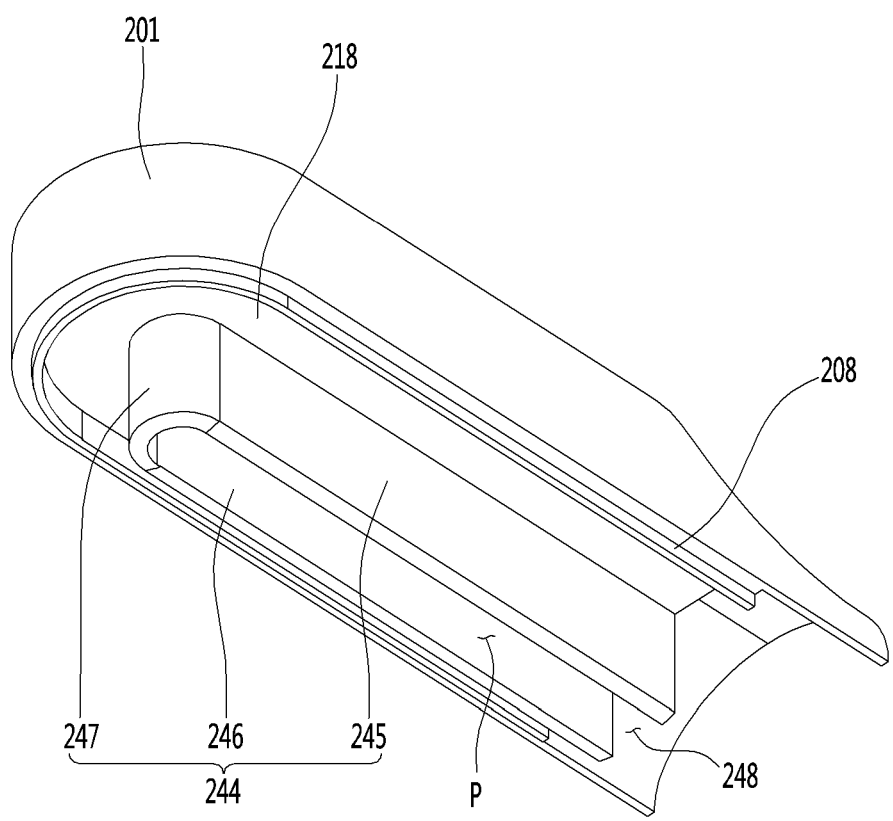
FIG. 8 is a perspective view of an upper body shown in a lower side.

The first coupler 240 may be provided with a head terminal 264, and the second coupler 530 may be provided with a handle terminal 582. When the second coupler 530 is inserted in the first coupler 240, the handle terminal 532 may be in contact with the head terminal 264. A contact between the handle terminal 532 and the head terminal 264 may allow the battery 540 in the handle 50 to power the light emitting device 223 in the head 20 (FIG. 7).

Referring to FIGS. 7 to 10, the head 20 may include a first and second frames or shells 200 and 250, a sterilizer 220, and a light diffuser 230 covering the sterilizer 220. The second frame 250 may be coupled to the first frame 200.

The first frame 200 may include a first space or recess 212 in which the sterilizer 220 is inserted and a second space P partitioned from the first space 212. The first space 212 may be provided to surround an upper or front portion of the second space P. Since the sterilizer 220 may be provided in the first space 212, the sterilizer 220 may surround the front portion of the second space P. Hair of the pet may flow into the second space P during use of the main body 10. Since the second space P may be partitioned from the first space 212, hair flowing into the second space P may be prevented from entering the first space 212. The sterilizer 220 positioned in the first space 212 may be prevented from contacting pet hair.

The first frame 200 may include an outer body 201 and an inner body 210 positioned in an inner region of the outer body 201. At least a portion of the outer body 201 may be formed in a shape corresponding to the inner body 210 to surround the outer side of the inner body 210. The first space 212 may be formed between the outer and inner bodies 201 and 210. The outer body 201 and the inner body 210 may be connected by a support wall 218. The first space 212 and the support wall 218 may define a recess or groove in which the sterilizer 220 is installed and that the light diffuser 230 covers.

The inner body 210 may be formed in an ellipse or stadium shape to form a first opening 214. The first opening 214 of the inner body 210 may serve as an inlet of the second space P.

Figure 9:
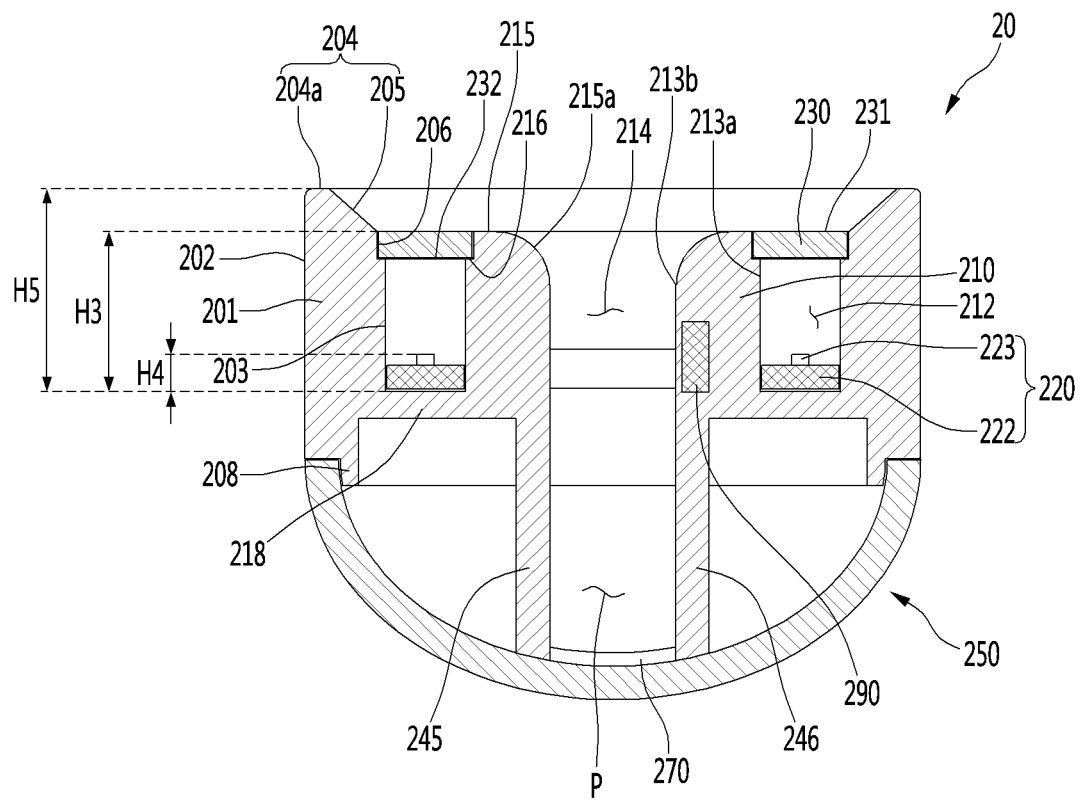
FIG. 9 is a cross-sectional view taken along line A-A of FIG. 3.

Although FIG. 9 shows the head 20 having an orientation such that the light emitting device 223 pointing upward, one of ordinary skill in the art should appreciate that, during use, the head 20 may often have an orientation that is opposite the orientation shown in FIG. 9 so that the light emitting device 223 points downward.

The support wall 218 may be a lower or back wall of the first space 212. The support wall 218 may extend in a horizontal direction between lower or back ends of the inner and outer bodies 210 and 201. The sterilizer 220 may be mounted on an upper or front surface of the support wall 218.

A height H3 from an upper or front surface of the support wall 218 to an upper or front end of the inner body 210 may be formed to be higher than a height H4 of the sterilizer 220. When the sterilizer 220 is seated on the support wall 218, an uppermost or front most end of the sterilizer 220 (i.e., the front of the light emitting device 223) may be spaced apart from the front end of the inner body 210.

A height H5 from the front of the support wall 218 to a front or upper end of the outer body 201 may be formed to be higher than the height H3 of the inner body 210. The outer body 201 may include an outer circumferential surface 202, an inner circumferential surface 203, and a connection surface 204 connecting the outer circumferential surface 202 and the inner circumferential surface 203. The outer circumferential surface 202 of the outer body 201 may form an appearance of the head 20. The inner circumferential surface 203 of the outer body 201 may form the first space 212. The connection surface 204 may form a front surface of the outer body 201.

A height from the support wall 218 to a front end of the outer circumferential surface 202 of the outer body 201 may be higher than a height from the support wall 218 to a front end of the inner circumferential surface 203 of the outer body 201. The connection surface 204 may include a horizontal surface 204a and an inclined surface 205. The horizontal surface 204a may extend in a horizontal direction from the outer circumferential surface 202 of the outer body 201 toward the inner circumferential surface 203. The inclined surface 205 may extend from an inner end of the horizontal surface 204a toward the inner circumferential surface 203.

A first support groove 206 may be formed on the inner circumferential surface 203 of the outer body 201 to support the light diffuser 230. Since the light diffuser 230 may be seated in the first support groove 206 within the inner circumferential surface 204, the light diffuser 230 may be spaced apart or separated from the outer circumferential surface 202 of the outer body 201.

The inner body 210 may include an outer circumferential surface 213a and an inner circumferential surface 213b. The outer circumferential surface 213a of the inner body 210 may form the first space 212. The inner circumferential surface 213b of the inner body 210 may form the first opening 214.

The inner body 210 may include a connection surface 215 connecting a front or upper end of the outer circumferential surface 213a and a front or upper end of the inner circumferential surface 213b. A second support groove 216 may be formed in the outer circumferential surface 213a of the inner body 210 to support the light diffuser 230.

An outer or front surface 231 of the light diffuser 230 may be flush with a front surface of the inner body 201 when the light diffuser 230 is supported by the first support groove 206 and the second support groove 216. A portion of the connection surface 215 may be adjacent to and flush with the light diffuser 230.

The light diffuser 230 may be further fused in the first support groove 206 and the second support groove 216 to be secured to the first frame 200. By fusing the light diffuser 230, it may be possible to prevent liquid from flowing into the first space 212.

Since the first and second support grooves 206 and 216 are spaced further backward than the horizontal surface 204a of the outer body 201, the light diffuser 230 may be protected from hitting a surface on which the head 20 rests or is applied. A position of the light diffuser 230 and the light emitting device 223 of the sterilizer 220 may be configured to protect the light diffuser 230 and sterilizer 220 from an external impact. In addition, a space between the light emitting device 223 and the light diffuser 230 may be configured to maximize an irradiation area of light emitted through the light diffuser 230.

The connection surface 215 of the inner body 210 may include an inclined or curved surface 215a inclined or curved from the outer circumferential surface 213a to the inner circumferential surface 213b. The curved surface 215a may be a round surface or inclined downward or backward from the outer circumferential surface 213a toward the inner circumferential surface 213b.

When the main body 10 is used while the head 20 is in contact with the skin of the pet, the horizontal surface 204a may contact the pet skin, while the light diffuser 230 may not contact the pet skin. As a contact area is increased via an increase in a size of the horizontal surface 204a, light emitted from the sterilizer 220 may be concentrated on the skin of the pet. Since the outer body 201 may include the inclined surface 205, when the main body 10 is used so that the head 20 is in contact with the skin of the pet, the inclined surface 205 may also be used to increase a contact area between the head 20 and the skin of the pet.

Light irradiated from the sterilizer 220 may be concentrated on the skin of the pet without leaking or escaping to an outside of the outer body 201. Since the light diffuser 230 may be provided to be spaced inwardly or backward from the front end of the outer body 201, the light diffuser 230 may be prevented from coming into direct contact with the skin of the pet. Light may be prevented from concentrating on one point or area of the skin of the pet. In addition, even if the main body 10 is placed on a resting surface or floor, the light diffuser 230 may not contact the resting surface, preventing damage to the light diffuser.

Since an inner or back surface 232 of the light diffuser 230 facing the light emitting device 223 may be spaced apart from the sterilizer 220, an irradiation angle of light from the light emitting device 223 may be increased until reaching the light diffuser 230 and then uniformly transmitted throughout the light diffuser 230. An area of light reaching the skin of the pet may be increased.

Since the front end of the inner body 210 is located inside and further back than the front end of the outer body 201, hair or fur separated from the pet may be easily gathered into the first opening 214 to the second space P. The inclined surface 215a of the connection surface 215 may further guide hair, fur, or other debris into the second space P.

The first frame 200 may further include a space forming wall 244 extending from the inner body 210 toward the second frame 250. A back end of the space forming wall 244 may contact the second frame 250, and the second frame 250 may cover a back or lower end of the second space P. The space forming wall 244 and the second frame 250 may form the second space P.

The space forming wall 244 may include a pair of straight walls 245 and 246 extending in a straight line and a curved or connection wall 247 may connect first ends of the pair of straight walls 245 and 246. Second ends of the pair of straight walls 245 and 246 may be kept spaced apart. A second opening 248 may be formed in a space between the second ends of the pair of straight walls 245 and 246. The second opening 248 may also serve as an inlet to the second space P.

Figure 10:
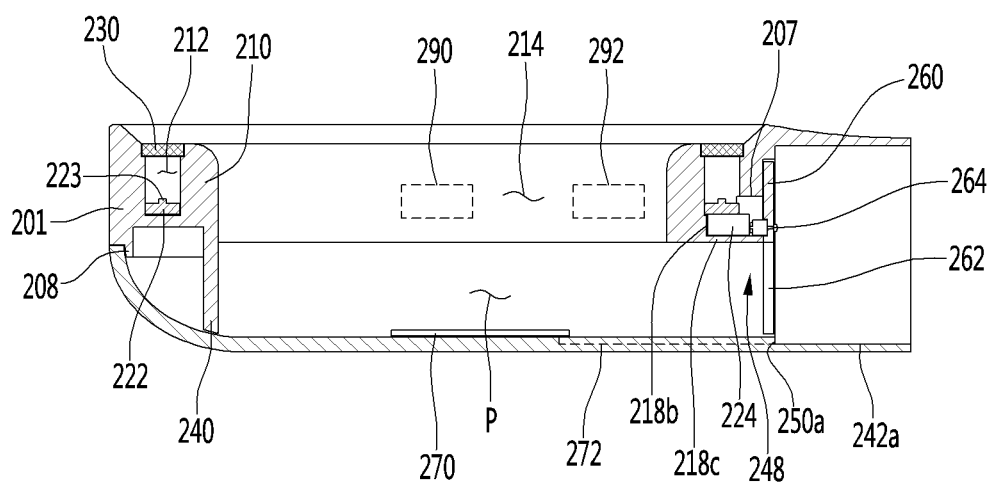
FIG. 10 is a cross-sectional view taken along line B-B of FIG. 5.

The first opening 214 may be an opening through which debris may flow in a vertical direction with respect to FIG. 10, while the second opening 248 may be an opening through which debris may flow in a lateral or horizontal direction with respect to FIG. 10. The second space P may have a bent shape. As an example, the second space P may have an "L" shape.

The second body 250 may include an ionizer 270 (e.g., plasma ionizer) to provide ions (e.g., plasma ions) to the second space P. The ions generated in the ionizer 270 may attach to or be coated on the hair or fur of the pet through the first opening 214 in the second space P.

When the plasma ions are coated on the hair of the pet, the hair may retain moisture and static electricity may be reduced so that fine dust, dander, or debris in the air may flow into the second space P instead of adhering to the pet hair. The ionizer 270 may be provided to face the first opening 214 and may receive power from the battery 540.

The sterilizer 220 may include a light emitting device printed circuit board (PCB) 222 and a plurality of light emitting devices 223 provided on a first (e.g., front or upper) surface of the light emitting device PCB 222. The plurality of light emitting devices 223 may be UV LEDs as described above. The plurality of light emitting devices 223 may further include a red LED.

The UV LED may irradiate light in the UVB or UVC wavelength bands. However, the wavelength band of the ultraviolet light emitted by the UV LED is not limited to the UVB or UVC wavelength band. In order to improve skin care treatment of the pet by the sterilizer 220, the light emitting device PCB 222 may be formed in an elliptic or stadium form to correspond to an overall elliptic or stadium shape of the first frame 200.

The light emitting device PCB 222 may be provided to surround the inner body 210, and may include an opening 222a in which the inner body 210 may be inserted. The plurality of light emitting devices 223 may be provided on the light emitting device PCB 222.

The light emitting device 223 may be installed or provided on a first (e.g., front or upper) surface of the light emitting device PCB 222 to face the light diffuser 230. The light emitting device PCB 222 may include a pair of curved or connection portions 222d and 222e connecting a pair of longitudinal portions or extensions 222b and 222c. 222e. Each of the longitudinal extensions 222b and 222c may extend in a straight line so that the light emitting device PCB 222 has a stadium shape. Alternatively, the longitudinal extensions 22b and 22c may have a curvature less than a curvature of the connection portions 22d and 222e to resemble a curved ellipse shape.

A length of each of the longitudinal extensions 222a and 222c may be longer than a length of each of the connection portions 222d and 222e. A plurality of light emitting devices 223 may be installed in each of the longitudinal extensions 222b and 222c. Although not limited, each of the longitudinal extensions 222b and 222c may be provided with ten or more light emitting devices 223. A plurality of light emitting devices 223 may also be installed at each of the connection portions 222d and 222e. A number of light emitting devices 223 provided in each of the longitudinal extensions 222b and 222c may be greater than a number of light emitting devices 223 provided in the connection portions 222d and 222e. For example, the number of light emitting devices 223 installed in each of the longitudinal extensions 222b and 222c may be twice or more the number of light emitting devices 223 provided in the connection portions 222d and 222e.

The light emitting devices 223 provided in each of the connection portions 222d and 222e may include a first light emitting device 223a and a second light emitting device 223b positioned adjacent to each of the longitudinal extensions 222b and 222c. At least one third light emitting device 223c may be positioned between the first and second light emitting devices 223a and 223b. As shown in FIG. 7, a plurality of third light emitting devices 223c are provided between the first and second light emitting devices 222a and 222b so that an intensity of light emitted from each of the connection portions 222d and 222e may be increased. FIG. 7 shows three third light emitting devices 222c, but embodiments disclosed herein are not limited to three third light emitting devices 223c.

Since the light emitting device PCB 222 may be formed in an elliptic or stadium shape, the plurality of light emitting devices 223 may also be arranged in an elliptic or stadium arrangement. The light emitting devices 223 may be spaced apart from each other to surround the inner body 210.

The sterilizer 220 may include a first connector 224 connected to the light emitting device PCC 222. The first connector 224 may be connected to a second (e.g., back or lower) surface of the light emitting device PCB 222, the second surface being opposite to the first surface on which the light emitting devices 223 are installed.

The first connector 224 may be connected to a connection portion 222d positioned adjacent to the handle 50 among the pair of connection portions 222d and 222e of the light emitting device PCB 222.

An accommodating portion or recess 218b may be formed in the support wall 218 to position the first connector 224. The first connector 224 may be silicon coated. A waterproof layer may be formed on an outer side of the first connector 224 by the silicon coating.

The support wall 218 may further include a cover wall 218c covering the first connector 224 positioned in the accommodation portion 218b. The cover wall 218c may connect the pair of straight walls 245 and 246 of the space forming wall 244. When the waterproof layer of the first connector 224 is present, the cover wall 218c may be omitted.

The outer body 201 may further include a slot 207 through which the first connector 224 may pass. The head 20 may further include a slot cover 260 that covers the slot 207. The slot cover 260 may include a hole or opening 262 that communicates with the second opening 244 of the second space P. The hole 262 may be aligned with the second opening 244 when the slot cover 260 covers the slot 207.

The slot cover 260 may be provided with a head terminal 264 connected to the first connector 224. When the handle 50 is connected to the head 20, the head terminal 264 may be in contact with the handle terminal 582. The slot cover 260 may further include a supply line or wire 268 to supply power to the ionizer 270. A power supply line 272 connected to the ionizer 270 may be provided in the second frame 250. The power supply line 272 may be connected to the supply line 268 when the slot cover 260 is coupled to the first coupler 240.

The second frame 250 may be provided to surround the space forming wall 244. The outer body 201 of the first frame 200 may be seated at an end portion of the second frame 250.

The first frame 200 and the second frame 250 may be fused or adhered together. A contact portion 208 of the first frame 200 (e.g., a flange or rib) may be fused or adhered to an inner surface of the second frame 250. A size of the contact portion 208 may be configured such that a contact area between the first frame 200 and the second frame 250 is increased via a bonding force by fusion or adhesion. A shape of the contact portion 208 may be configured to correspond to a shape or inner contour of the second frame 250. When the first frame 200 and the second frame 250 are coupled, the first frame 200 may form a first part of the first coupler 240, and the second frame 250 may form a second part of the first coupler 240.

The slot cover 260 may be fused or adhered to the first frame 200 and the second frame 250 in the coupling space 242 of the first coupler 240. The contact part 208 may be formed along the circumference of the outer body 201 of the first frame 200.

The slot cover 260 may be formed with a seating portion or stepped portion 263 formed by recessing a portion of the slot cover 260 radially inward. The contact portion 208 may be provided in the stepped portion 263 so that the slot cover 260 does not interfere with the contact portion 208 in the coupling space 242.

The first coupler 240 may be provided with a mounting groove 242a in which the second coupler 530 may be inserted. The mounting groove 242a may be formed as a recessed portion of an inner surface of the second frame 250. The mounting groove 242a may define a side of the coupling space 240. A stopper or stepped portion 250a may be formed in the second frame 250 adjacent to the mounting groove 242a.

The second coupler 530 may be inserted into the coupling space 240 along the mounting groove 242a to contact the stopper 250a. When the second coupler 530 contacts the stopper 250a, a coupling between the first coupler 240 and the second coupler 530 may be complete.

The inner body 210 may include a care tool sensor or mounting sensor 290 (e.g., a Hall sensor) to detect a mounting of a care tool (e.g., 70, 80, or 90 in FIGS. 11-18), which will be described later with reference to FIGS. 11-18. The care tool sensor 290 may be oriented toward the first opening 214, where a care tool may be inserted. The care tool sensor 290 may include, for example, a hall sensor to detect a magnetic force. However, the care tool sensor 290 is not limited to a hall sensor, and may alternatively be a contact or touch sensor or a proximity sensor.

A care tool fixing portion 292 (e.g., a magnet or a metal) may be provided at a position spaced apart from the care tool sensor 290 in the longitudinal direction in the inner body 210. The care tool fixing portion 292 may include at least one of a metal and a magnet that interacts with at least one of a metal or a magnet provided in a fixing portion (e.g, first, second, or third fixing portions 724, 824, or 924 in FIGS. 11-18) of a care tool to be mounted. The care tool fixing portion 292 may be oriented to face the first opening 214. A care tool (70, 80, or 90) may be mounted to the main body 10 via the care tool fixing portion 292 and a fixing portion (724, 824, or 924) of the care tool. Details of the care tools will be described later with reference to FIGS. 11-18.

The handle 50 may include a handle body or frame 500. The handle body 500 may include the second coupler 530 to be coupled to the first coupler 240. The battery 540 may be provided inside the handle body 500. The battery 540 may be a secondary or auxiliary battery that may be charged by external power supplied from an external or commercial power source (e.g., wall socket).

The handle body 500 may include a first handle body or first shell 510 and a second handle body or second shell 520 coupled to the first shell 510. The handle body 500 may have an elliptical shape or cross-section so that a user may easily grip the handle.

The first shell 510 may be provided with a user interface or operation switch 516. The operation switch 516 may also be referred to as an input device. The operation switch 516 may be configured to be slidable in the longitudinal direction of the first shell 510. An operation or switch slot 512 extending in the longitudinal direction may be formed in the first shell 510 to allow sliding of the operation switch 516. A first portion of the operation switch 516 may be located inside the handle body 500, while a second portion may protrude out of the handle body 500 through the operation slot 512.

An on/off command of the sterilizer 220 may be input through the operation switch 516. Alternatively or in addition thereto, an intensity of the sterilizer 220 may be adjusted via the operation switch 516 when the sterilizer 220 is turned on, as well as an o/off command of the sterilizer 220.

The handle 50 may further include a battery support or case 543 that supports the battery 540. The battery case 543 may include a support frame 541. The support frame 531 may include an opening 542 that forms a space for the battery 540 to be provided. The battery case 543 may further include a plurality of support ribs 544 extending from the support frame 541 to support the battery 540 positioned in the opening 542 of the support frame 541.

The plurality of support ribs 544 may extend downward from the support frame 541 at opposite sides of the opening 542. The plurality of support ribs 534 may extend to be closer to each other toward a lower or back side. Each support rib 534 may be rounded with a same or similar curvature as the battery 540 so that the plurality of support ribs 534 may stably support the battery 540. The battery 540 may be seated on the rounded portions of the plurality of support ribs 534.

The handle 50 may further include a main PCB 552 connected to the battery 540 and a PCB holder 550 supporting the main PCB 552. The PCB holder 550 may be coupled to the battery case 543 at a position between the first shell 510 and the battery case 543. The main PCB 552 may be installed or provided in the PCB holder 550.

The handle 50 may include a plurality of sensors 556 (e.g., touch or contact sensors or proximity sensors) to sense an operation command of the operation switch 516. The plurality of sensors 556 may be spaced apart from each other in a sliding direction of the operation switch 516 (i.e., the longitudinal direction of the first shell 510). The plurality of sensors 556 may include a first sensor that receives or senses an off signal and a second sensor that receives or senses an on signal. The plurality of sensors 556 may be installed on the main PCB 552.

The handle 50 may include a proximity sensor 557 that includes a light emitting device and a light receiving device. The proximity sensor 557 may be installed or located on the main PCB 552. The proximity sensor 557 may sense a proximity to a pet or surface, and a controller on and/or electrically coupled to the main PCB 552 may determine how close the main body 10 is to the skin of the pet via the proximity sensor 557. When the proximity sensor 557 is provided on the handle 50, the proximity sensor 557 may be located in an upper side or portion of the handle 50 to be close to the head 20 to accurately detect a position or distance of a pet or surface to be treated. As an alternative, the proximity sensor 557 may be provided in the head 20 to more accurately determine a distance a pet may be away from the head 20, where the sterilizer 220 may be housed. In such a case, the proximity sensor 557 may be provided on the light emitting device PCB 222.

The first shell 510 may be provided with a hole 514 through which the light emitter of proximity sensor 557 may transmit light. A hole cover or transmissive membrane 518 may cover the hole 514. The hole 514 and the hole cover 518 may be provided between the second coupler 530 and the operation slot 512 to reduce a likelihood that a user's hand will cover the hole 514 or hole cover 518. The hole 514 and the hole cover 518 may be positioned closer to the head 20 than the operation switch 516.

The handle 50 may further include a gyro sensor 558. An up and down direction or orientation of the handle 50 may be determined through the gyro sensor 558. The gyro sensor 558 may be installed in the main PCB 552. A position of the operation switch 512 and/or the sterilizer 220 may be determined through an orientation sensed by the gyro sensor 558 to face upward or downward. The sterilizer 220 may be controlled based on the orientation sensed by the gyro sensor 558 and/or determined positions of the sterilizer 220 and/or the operation switch 512. Although FIG. 7 shows that the operation switch 512 is on a front of the handle 50 to face a same direction as the sterilizer, alternatively, the operation switch 512 may be on a back of the handle 50 so that a user may easily input an on/off command of the sterilizer 220 and/or adjust an intensity of the sterilizer 220 with a thumb while the sterilizer 220 is oriented downward. In such an alternative, when a controller 1910 (FIG. 19) determines that the operation switch 512 faces up via the gyro sensor 558, the controller may determine that the sterilizer 220 faces down.

The main PCB 552 may include a connection portion or tab 554, and the connection portion 554 may be connected to a second connector 537. The second connector 537 may transmit a control signal generated by the main PCB 522 and/or power supplied from the main PCB 522 to the head 20.

The handle 50 may further include an auxiliary or secondary PCB 560. The auxiliary PCB 560 may include or electrically couple to a controller to determine whether a care tool (70, 80, or 90) is mounted based on a signal output from the care tool sensor 290. The auxiliary PCB 560 may be fixed to the battery base 543 and/or provided on the back side of the main PCB 552.

The main PCB 520 and the auxiliary PCB 560 may be collectively referred to as a controller 1910 (FIG. 19), although each of the main PCB 520 and the auxiliary PCB 560 may have respective sub-controllers. The controller may discharge the battery 540 to supply power from the battery 540 to the sterilizer 220. The controller may adjust the power supply to the sterilizer 220 based on whether the tool care is installed or based on information sensed by the proximity and gyro sensors 557 and 558, in addition to the sensors 556.

The handle 50 may further include a charging PCB 565 to charge the battery 540.

The charging PCB 565 may include a first charging connector 565a and a second charging connector 565b. The first charging connector 565a may be connected to a base terminal provided in the base 60 to receive a charging voltage. When the handle 50 is seated on the base 60, the first charging connector 565a and the base terminal may contact each other to allow the battery 540 to be charged. The second charging connector 565b may be, for example, a second terminal or a port (e.g., USB port) that is connected to a charging cable (e.g., USB charging cable). The USB charging cable may be connected to an outlet or a device for power supply. When the USB charging cable is connected to the second charging connector 565b, the battery 540 may be charged even when the main body 10 is in use.

The charging PCB 565 may be installed in a PCB installation unit 545 provided in the battery case 543. Each of the charging connectors 565a and 565b may pass through holes 573 and 574 formed in a first or bottom cover 570 provided on a lower or bottom end of the handle 50. Alternatively, any one of the first charging connector 565a and the second charging connector 565b may be omitted.

A receiver for wireless charging may be provided inside or outside the PCB installation unit 535. The receiver may include a receiving coil. The receiver may be connected to the charging PCB 565, the battery 540 may be supplied with power through the respective charging connectors 565a and 565b or wirelessly charged (via, e.g., a wireless power transmission or WPT method) through the receiver. A transmitter to transmit power to the receiver may be provided in a separate storage device, a charging pad, etc.

Alternatively, both the first charging connector 565a and the second charging connector 565b may be omitted, and the handle 50 may include only a wireless charging receiver. As another alternative, the handle 50 may include any one of a wireless charging receiver, the first charging connector 565a and the second charging connector 565b.

When the first shell 510 and the second shell 520 are coupled, top and bottom ends of the handle body 500 may be opened. The handle 50 may include a first cover 570 and a second cover 580 that cover bottom and top openings, respectively, of the handle body 500. The first cover 570 may cover a bottom opening of the handle body 500 at an end of the handle 50 that is inserted into and/or connected to the base 60. The second cover 580 may cover the second coupler 530.

The first cover 570 may include a connector slot 574 through which the charging connector 565a passes. The second cover 580 may include the handle terminal 582. The handle terminal 582 may be connected to the second connector 537.

A method of managing the skin of the pet using the main body 10 will be described. The user may grip the handle 50 and aim the light diffuser 230 of the head to face the pet so that light from the sterilizer 220 is emitted toward the pet.

Regardless of a position or orientation of the main body 10, a user may input a command to operate the sterilizer 220 via the operation switch 516. When the on command of the operation switch 516 is input, the controller may determine whether an on condition of the sterilizer 220 is satisfied without immediately turning on the sterilizer 220. When the on condition of the sterilizer 220 is satisfied, the controller may turn on the sterilizer 220.

The on condition of the sterilizer 220 may be satisfied when the controller determines, based on a sensed orientation by the gyro sensor 558, that the sterilizer 220 faces downward and also determines, based on a sensed distance by the proximity sensor 557, that a pet is a predetermined distance away or less. The controller may determine that the sterilizer 220 faces downward by determining that the operation switch 512 and/or gyro sensor 558 faces downward (as shown in the embodiment of FIG. 7) or alternatively, in an embodiment where the operation switch 512 and gyro sensor 558 are on a side of the main body 10 opposite to a side the sterilizer 220 is provided, that the operation switch 512 and/or gyro sensor 558 faces upward.

The sterilizer 220 may not be turned on unless the head 20 and/or the main body 10 is close to the pet and when the sterilizer 220 is pointed downward so as not to unnecessarily irradiate UV radiation, which may be damaging or fatiguing to a user's eyes. A control operation of the sterilizer 220 may be configured to prevent the sterilizer 220 from being turned on when the light diffuser 230 of the head 20 faces upward. Even when the light diffuser 230 of the head 20 is directed downward, when the light diffuser 230 of the head 20 is not close to the skin of the pet, the sterilizer 220 may be prevented from being turned on unnecessarily.

In an alternative control operation, when the on command of the operation switch 516 is input, the controller may control the sterilizer 220 to emit light at a first intensity, either by controlling a number of light emitting devices 223 to turn on or by controlling intensities of the light emitting devices 223. When a normal condition is satisfied, the controller may control the sterilizer 220 to irradiate light with a second intensity greater than the first intensity. To achieve the second intensity, the controller may control more of the light emitting devices 223 to turn on. In this case, the "normal condition" is the same as the "on condition" previously described above.

In either control method, when the on command is input via the operation switch 516, the controller may control a red or other colored light emitting device among the plurality of light emitting devices 223 to turn on so that the user may be informed that the on command was input. Such a light emitting device may be called an "output light emitting device" or "information light emitting device", and may be a light emitting device (e.g., LED) that emits light in a visible wavelength range.

Hereinafter, various types of care tools that can be used in combination with the main body 10 will be described.

Figure 13:
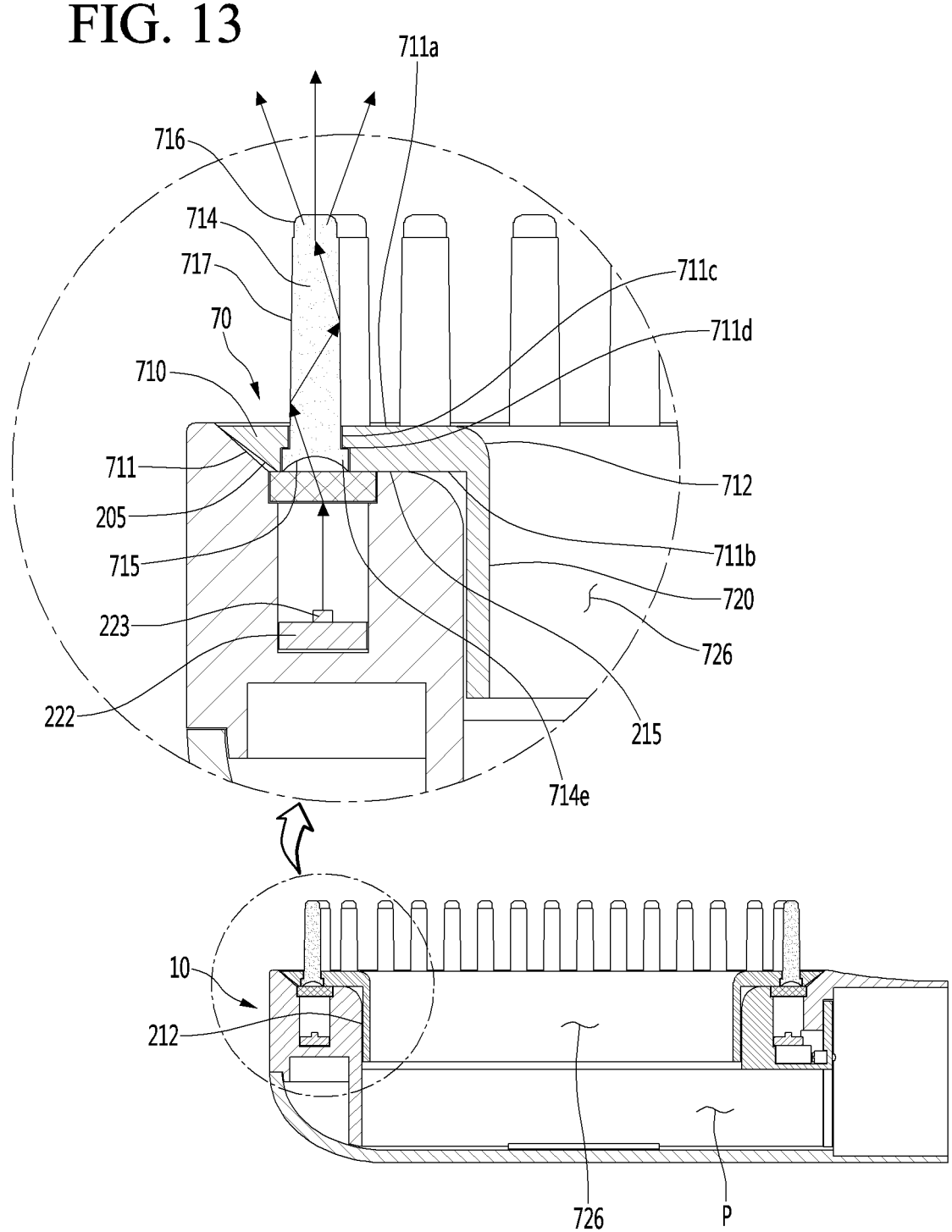
FIG. 13 is a cross-sectional view taken along line E-E of FIG. 12.

Referring to FIGS. 11 to 13, a first care tool 70 may be detachably coupled to the head 20 of the main body 10.

When the first care tool 70 is coupled to the head 20, light emitted from the sterilizer 220 may be emitted through the first care tool 70 to be transmitted at an end of the tool 70.

The first care tool 70 may include a plate-shaped tool body 710 and a head coupler 720 extending from the tool body 710 that couples to the head 20. The tool body 710 may be formed in an ellipse or stadium shape, and may include an opening 712 in the shape of a stadium or an ellipse.

The first care tool 70 may include a plurality of protrusions or teeth 714 protruding from the tool body 710 in a direction opposite a direction in which the head coupler 720 extends. The teeth 714 may also be referred to as light transmitters or light focusers, and may serve to simulate a pet's skin and/or comb a pet's hair. The plurality of teeth 714 may be provided to surround the opening 712 in the tool body 710.

The tool body 710 may include a pair of longitudinal extensions 710a and 710b and a pair of curved or connection portions 710c and 710d connecting the pair of longitudinal extensions 710a and 710b. Each of the longitudinal extensions 710a and 710b may extend in a straight line, or alternatively may be curved. A length of each of the longitudinal extensions 710a and 710b may be longer than a length of each of the connection portions 710c and 710d. The longitudinal extensions 710a and 710b may be shaped to correspond to the longitudinal extensions 222b and 222c of the light emitting device PCB 222, and the connection portions 710c and 710d may correspond to the connection portions 222d and 222e of the light emitting device PCB 222.

The plurality of teeth 714 may extend from each of the longitudinal extensions 710a and 710b and from each of the connection portions 710c and 710d. A number of teeth 714 provided in each of the longitudinal extension portions 710a and 710b may be larger than a number of teeth 714 provided in the connection portions 710c and 710d. The teeth 714 provided in the connection portions 710c and 710d may include a first protrusion or tooth 714a and a second protrusion or tooth 714b positioned adjacent to each of the longitudinal extension portions 710a and 710b. At least one third protrusion or tooth 714b may be provided between the first and second teeth 714a and 714b. A plurality of third teeth 714c may be provided between the first and second teeth 714a and 714b. For example, in FIG. 11, three third teeth 714c are provided.

Each of the plurality of teeth 714 may align with a light emitting device 223 of the sterilizer 220 when the first care tool 70 is coupled to the head 20. The number of teeth 714 may be less than or equal to a number the light emitting devices 223 of the sterilizer 220 so that every tooth 714 aligns or overlaps with at least one light emitting device 223. Light irradiated from each light emitting device 223 of the sterilizer 220 may be irradiated to each of the plurality of teeth 714 of the first care tool 70.

The plurality of teeth 714 may be integrally formed with the tool body 710. In this case, the plurality of teeth 714 may protrude from a first surface 711a of the tool body 710. A light condensing surface or lens 715 to focus or collect light emitted from each of the light emitting devices 723 may be provided at portions of a second surface 711b of the tool body 710 corresponding to the plurality of teeth 714. The light collecting surface 715 may be formed to be recessed from the second surface 711b toward the first surface 711a.

The light collecting surface 715 is a concave surface. A number of light collecting surfaces 715 may be equal to the number of teeth 714.

Alternatively, as exemplified in FIG. 13, the plurality of teeth 714 may be manufactured separately from the tool body 710 and coupled to the tool body 710. In this case, the tool body 710 may further include a hole 711c penetrating through the first surface 711a and the second surface 711b. The plurality of teeth 714 may protrude out of the first surface 711a through the holes 711c from behind the second surface 711b. Each tooth 714 may include a stepped portion 714e having a larger diameter or width than the rest of the tooth 714, and the tool body 710 may have a corresponding stepped or locking portion 711d formed in the hole 711c to engage with the stepped portion 714e of the tooth 714. The light collecting surface 715 may be formed on a surface of each tooth 714 facing the light diffuser 230. The light collecting surface 715 may be formed to be recessed in a direction away from the light diffuser 230 to be a concave surface.

When the plurality of teeth 714 are integrally formed with the tool body 710, the plurality of teeth 714 and the tool body 710 may be formed of a light transmissive material (transparent or translucent). A light transmissive material may mean a material through which UV radiation or other electromagnetic readiation may be transmitted. A light blocking and/or reflective coating layer 717 may be formed or coated on the plurality of teeth 714 and the tool body 710. When the plurality of teeth 714 are formed separately from the tool body 710, the tool body 710 may be formed of a light blocking or opaque material while the plurality of teeth 714 may be formed of a light transmissive material. The light blocking coating layer 717 may be coated on the teeth 714.

The coating layer 717 may block or shield light emitted from the sterilizer 220. The coating layer 717 may also reflect light inside of the teeth 714. End portions of the plurality of teeth 714 may be laser engraved to remove the coating layer 717 to define transmission ends 716. The light irradiated from the sterilizer 220 may be reflected by the coating layer 717 on the plurality of teeth 714 and guided to the transmission end 716 to pass through the transmission end 716 and ultimately to the pet skin.

The plurality of teeth 714 may have a predetermined length that is long enough for the transparent end 716 to contact pet skin under a layer of pet fur or hair. Light may be irradiated to and focused on the skin of the pet to treat and simulate the pet skin, while a back portion of the teeth 714 not contacting the pet skin may serve to comb the pet hair or fur. The user may grip the handle 50 and guide the head 20 along a surface of the pet to comb the pet hair using the teeth 714 and treat the pet skin via the transmission end 716.

The head coupler 720 may protrude from the second surface 711b of the tool body 710 along a circumference of the opening 712. The head coupler 720 may be formed in an ellipse or stadium shape and may include a tool space 726 communicating with the opening 712. The head coupler 720 may be formed in a shape corresponding to the inner body 210 of the first frame 200, and may be inserted into the first opening 214 of the inner body 210. When the head coupler 720 is inserted into the inner body 210 of the first frame 200, the tool space 726 of the head coupler 720 may communicate with the second space P. When the main body 10 is used with the first care tool 70, hair may be separated from the pet and guided to the second space P of the head 20 via the opening 712 and the tool space 726 of the first care tool 70.

Since the head coupler 720 may be inserted into and provided in the inner body 210 of the first frame 200, the inner body 210 may also be referred to as a tool coupler.

The first care tool 70 may include a first magnet 722, and a first fixing portion 724, which may also include a metal or a magnet. The first magnet 722 may provide a magnetic force sensed by the care tool sensor 290, while the first fixing portion 724 may provide a magnet force to secure the first care tool 70 to the care tool fixing portion 292 of the head 20.

The first magnet 722 may be located at a position facing the care tool sensor 290 of the inner body 210 when the head coupler 720 is coupled to the inner body 210. The first magnet 722 may have a first magnetic force. The controller may determine that the first care tool 70 is mounted on the main body 10 when a magnitude of magnetic force sensed by the care tool sensor 290 is equal to the first magnetic force. When the controller determines that the first care tool 70 is mounted and/or that an on condition has been satisfied, the controller may control the sterilizer 220 to turn on the plurality of light emitting devices 223. Alternatively or in addition thereto, the controller may supply power to the ionizer 270 to operate the ionizer 270.

The first fixing portion 724 may include a magnet or a metal. When a metal is provided in the care tool fixing portion 292, the first fixing portion 724 may be provided with a magnet that attracts the metal. Alternatively, when a magnet is provided in the care tool fixing portion 292, a magnet or a metal may be provided in the first fixing portion 724 to attract the magnet of the care tool fixing portion 292. In the case where both the care tool fixing portion 292 and the first fixing portion 724 have magnets, the magnet of the care tool fixing portion 292 may have a first pole or polarity, and the magnet of the first fixing portion 724 may have a second pole or polarity opposite the first pole or polarity. When the head coupler 720 is inserted into the inner body 210, the care tool fixing portion 292 and the first fixing portion 724 may secure a coupling of the first care tool 70 to the head 20.

The tool body 710 may be provided in a space formed by the height difference between the outer body 201 and the inner body 210. The tool body 710 may be seated on the connection surface 215 of the inner body 210. The tool body 710 may include an inclined surface 711 that contacts the inclined surface 205 of the outer body 201.

The first care tool 70 may be pulled and separated from the head 20. The handle 50 may be further pulled and separated from the head 20 so that hairs gathered in the second space P of the head may be easily discharged through the first opening 214 and the second opening 248.

Figure 16:
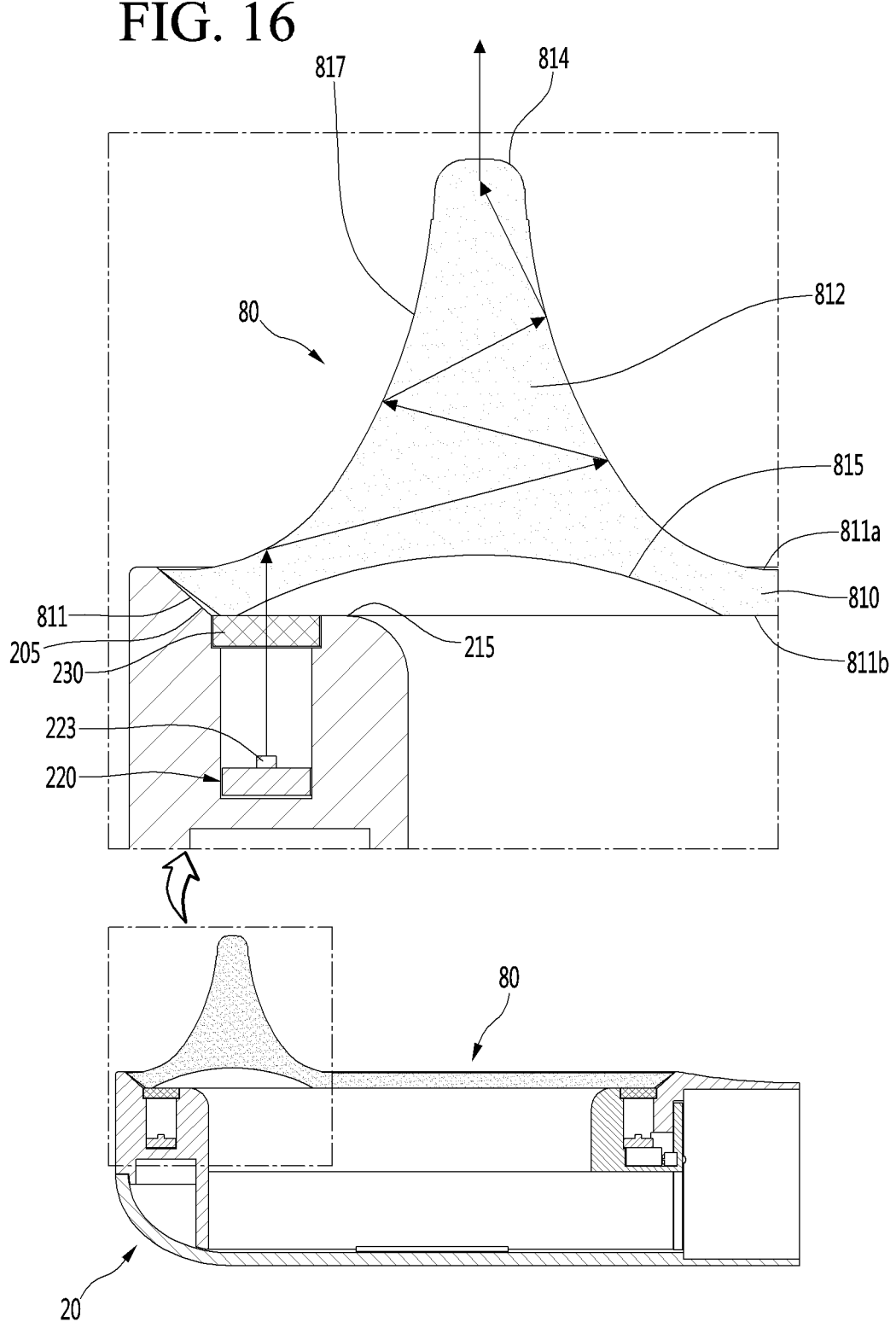
FIG. 16 is a cross-sectional view taken along line F-F of FIG. 15.

Referring to FIGS. 14-16, the second care tool 80 may be detachably coupled to the head 20 of the main body 10. The second care tool 80 may be, for example, an otoscope to manage and/or treat an ear of the pet. The second care tool 80 may be configured to emit intense light from a concentrated area.

The second care tool 80 may include a plate-shaped tool body 810 and a head coupler 820 extending from the tool body 810 to couple to the head 20. The tool body 810 may be formed in an elliptic or stadium shape.

The tool body 810 may include a first end 810a and a second end 810b opposite the first end 810 in a longitudinal direction. The tool body 810 may include a first surface 811a and a second surface 811b opposite to first surface 811a.

The first surface 811a of the tool body 810 may be provided with an insertion portion or probe 812 protruding outward. The insertion portion 812 may protrude in a direction away from the second surface 811b on the first surface 811a. The insertion portion 812 may be formed to have a trumpet or trapezoidal cross-section having a receding width or diameter that decreases away from the first surface 811a.

A part of the insertion portion 812 may be inserted into an ear of the pet, and may have a shape configured to fit inside of an ear or ear canal. The insertion portion 812 may be located closer to the first end 810a than the second end 810b on the first surface 811a of the tool body 810. Although not limited, if a bisecting line L that bisects the first end 810a and the second end 810b of the tool body 810 is provided, the insertion portion 812 may be located closer to the first end 810A than the line L.

The tool body 810 may be provided in the space formed by the height difference between the outer body 201 and the inner body 210. The tool body 810 may include an inclined surface 811 that contacts the inclined surface 205 of the outer body 201. The first surface 811a of the tool body 810 may be a front surface that faces an outside and the second surface 811b of the tool body 810 may be a back surface that faces the inner body 210 and the light diffuser 230.

A light collecting surface or lens 815 may be formed on the second surface 811b at a portion of the tool body 810 corresponding to the insertion portion 812. The light collecting surface 815 may be formed to be recessed in a direction away from the light diffuser 230 to be a concave surface. A portion of the light collecting surface 815 may overlap with the light guide 230 so that light emitted by the light emitting device 223 and passing through the light diffuser 230 may also pass through the light collecting surface 815.

The tool body 810 and the insertion portion 812 may be formed of a light transmissive material. A light blocking or reflective coating layer 817 may be formed on the outer surface of the tool body 810 and the insertion portion 812. An end portion of the insertion portion 812 may be laser engraved to remove the coating layer 817 to form a transmission end 814.

Light irradiated from the sterilizer 220 may be reflected by the coating layer 817 in the insertion portion 812 and guided to the transmission end 814 to be passed through the transmission end 814. The transmissive end 814 of the insertion portion 812 may be inserted into the ear of the pet, and the light transmitted through the transmissive end 814 may be guided and/or focused into the ear of the pet to manage and treat the ear.

The second care tool 80 may include a second magnet 822 and a second fixing portion 824 similar to the first magnet 722 and first fixing portions 724. The second magnet 822 may be located at a position that faces the care tool sensor 290 of the inner body 210 when the head coupler 820 is coupled to the inner body 210.

The second magnet 822 may have a second magnetic force different in magnitude from the first magnetic force. The controller may determine that the second care tool 80 is mounted on the main body 10 when a magnitude of magnetic forced sensed by the care tool sensor 290 is equal to the second magnetic force. When the controller determines that the second care tool 80 is mounted and/or that an on condition is satisfied, the controller may control the sterilizer 220 such that only some of the plurality of light emitting devices 223 are turned on. As an example, only the light emitting device 223 positioned behind or adjacent to the insertion portion 812 and/or the light collecting surface 817 may be turned on.

Even if all of the plurality of light emitting devices 223 are turned on, light irradiated from all of the plurality of light emitting devices 223 may not pass through the transmission end 816 of the insertion unit 812. As such, when all of the plurality of light emitting devices 223 are turned on while the second care tool 80 is mounted, there may be unnecessary power consumption. However, when the controller only controls the plurality of light emitting devices 223 behind the light collecting surface 815 to be turned on when the controller determines that the second care tool 80 is mounted, unnecessary power consumption may be prevented.

The head coupler 820 may include a second fixing portion 824 to interact with the care tool fixing portion 292 of the inner body 210. The second fixing portion 824 may include a magnet or a metal to interact with a magnet or metal of the care tool fixing portion 292. When both the second fixing portion 824 and the care tool fixing portion 292 have magnets, the magnet of the care tool fixing portion 292 may have a first pole or polarity, and the magnet of the head coupler second fixing portion 824 may have a second pole or polarity opposite the first pole or polarity.

Figure 17:
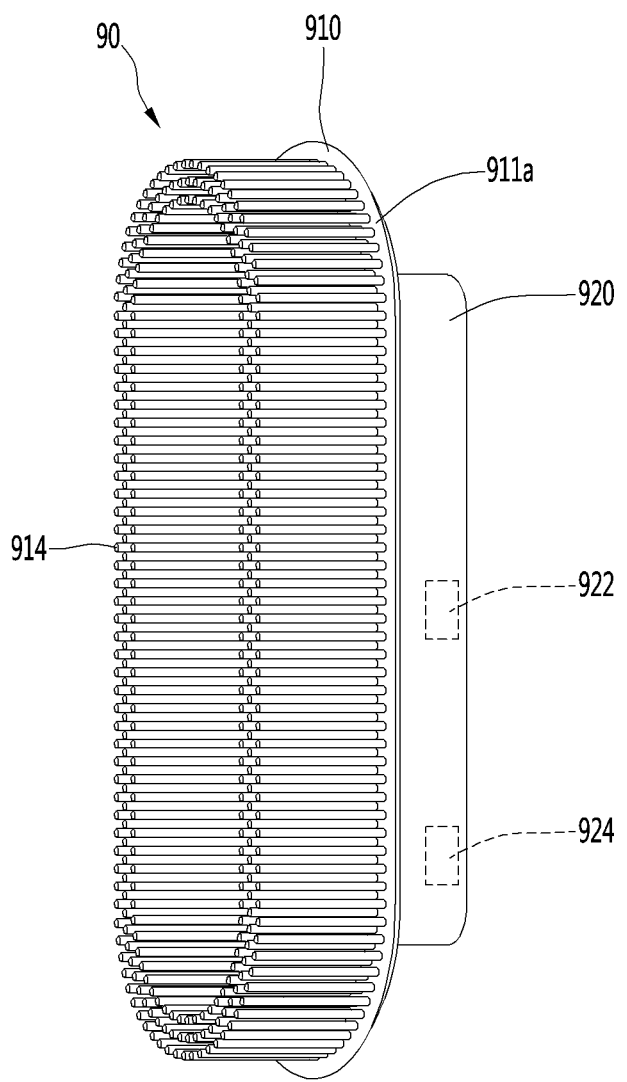
FIG. 17 is a perspective view of a third care tool.
Figure 18:
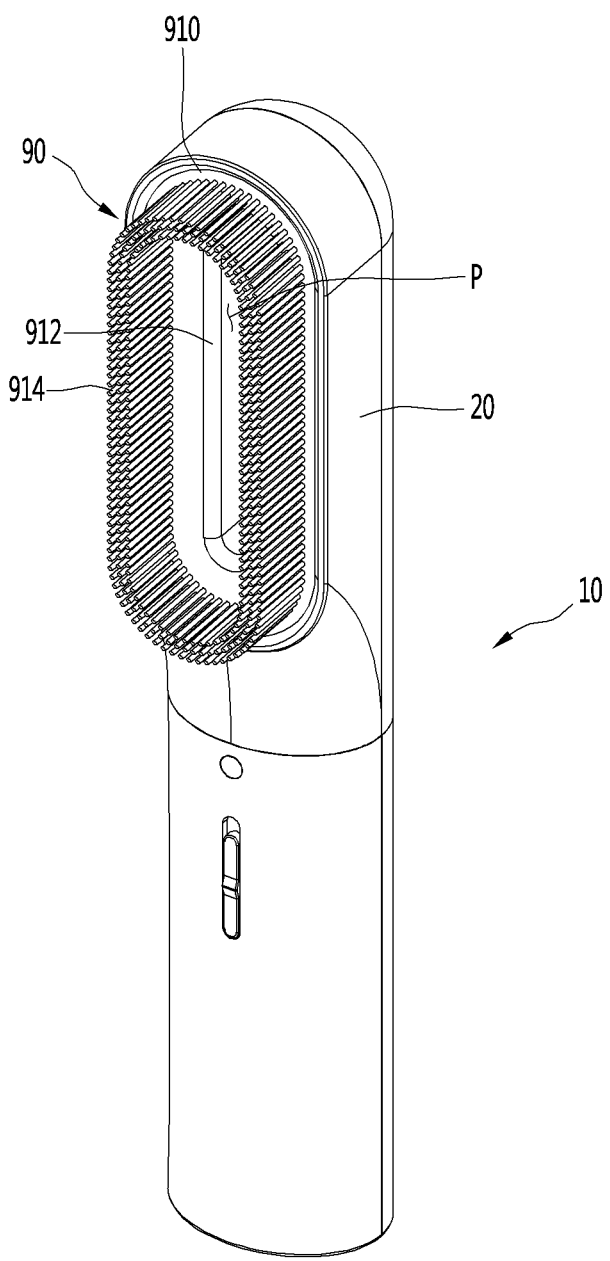
FIG. 18 is a perspective view illustrating a state in which the third care tool is coupled to a main body.

Referring to FIGS. 17 to 18, the third care tool 90 may be detachably coupled to the head 20 of the main body 10. The third care tool 90 may be used to manage pet fur hair by combing or brushing the pet hair. The third care tool 90 may be optionally used with a vacuum cleaner to suction hair collected in the second space P of the inner body 210.

The third care tool 90 may include a plate-shaped tool body 910 and a head coupler 920 extending from the tool body 910 to couple to the head 20.

A structure of the tool body 910 and the head coupler 920 of the third care tool 90 may be substantially the same or similar to a structure of the tool body 710 and the head coupler 720 of the first care tool 70. For example, the tool body 910 may be formed in an elliptic or stadium shape.

The tool body 910 may include a first surface 911a and a second surface 911b opposite to the first surface 911a. A plurality of brush protrusions or bristles 914 protruding outward may be provided on the first surface 811a of the tool body 910. The plurality of bristles 914 may be arranged in an ellipse form. A group of bristles 914 may be referred to as a brush group. A plurality of brush groups may be provided on the first surface 811a of the tool body 910 and arranged in an ellipse form.

The tool body 910 may be provided with an opening 912 through which hairs separated from the pet may pass. The head coupler 920 may extend from the second surface 911b of the tool body 910. The head coupler 920 may be coupled to the inner body 210 of the head 20.

Like the first and second care tools 70 and 80, the third care tool 80 may include a third magnet 922 and a third fixing portion 924. The third magnet 922 may be located in the head coupler 920 at a position facing the care tool sensor 290 of the inner body 210 when the head coupler 920 is coupled to the inner body 210. The third magnet 922 may have a third magnetic force different in magnitude from the first magnetic force and the second magnetic force. The controller may determine that the third care tool 90 is mounted on the main body 10 when the care tool sensor 290 senses a magnitude of magnetic force equal to the third magnetic force. When the controller determines that the third care tool 90 is mounted to the head 20, the controller may control the sterilizer 220 to turn off all of the plurality of light emitting devices 223.

The bristles 914 and the third care tool body 910 may not be formed of a light transmissive material. The sterilizer 220 may not operate when the third care tool 90 is in use to prevent an unnecessary power consumption.

When it is determined that the third care tool 90 is mounted to the head 20, the controller may supply power to the ionizer 270 to operate the ionizer 270. Ions may be emitted out of the first opening 214 and opening 912 of the third care tool 90, and the bristles 914 may help to coat the ions on a surface of the pet hair.

The head coupler 920 may include a third fixing portion 924 to interact with the care tool fixing portion 292 of the inner body 210. The third fixing portion 924 may include a magnet or a metal that attracts to a magnet or metal in the care tool fixing portion 292. When both the third fixing portion 924 and the care tool fixing portion 292 have magnets, the magnet of the care tool fixing portion 292 may have a first pole or polarity, and the magnet of the third fixing portion 924 may have a second pole or polarity opposite to the first pole or polarity. As shown in FIG. 18, when the third care tool 90 is coupled to the head 20 and used, the hair 20 separated from the pet may be drawn through the opening 912 of the third care tool 90 and into the second space P.

Figure 19:
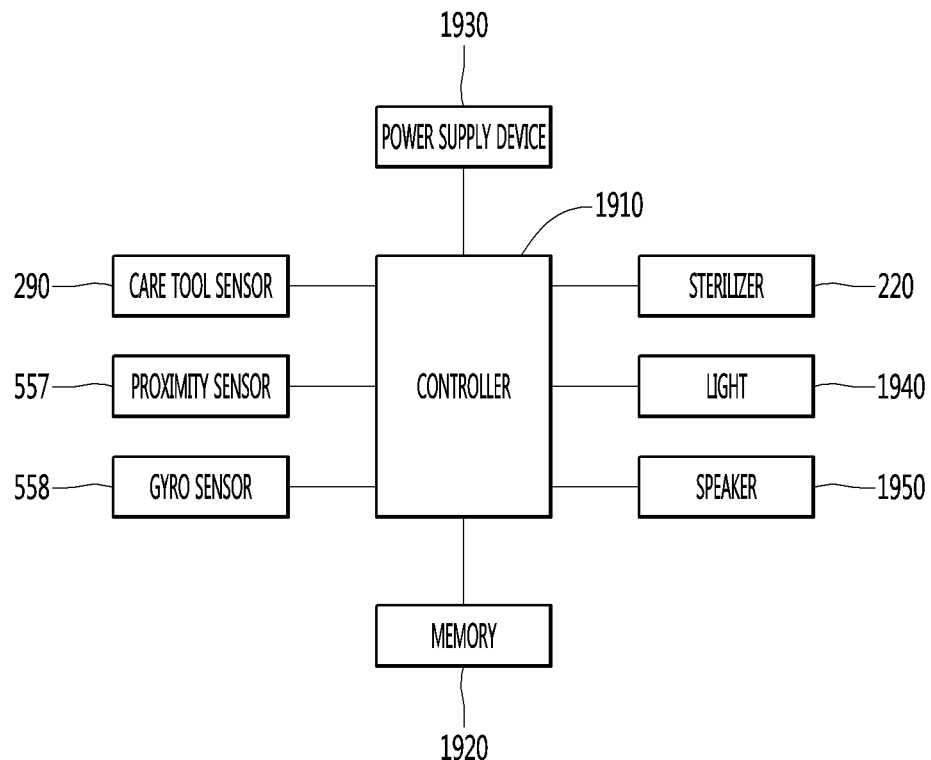
FIG. 19 is a schematic block diagram of a control configuration included in a main body of a pet care device according to an embodiment.

Referring to FIG. 19, the main body 10 may include a controller 1910, a memory 1920, and a power supply device 1930. As described above with reference to FIG. 7, the controller 1910 may collectively refer to the main PCB 552 and the auxiliary PCB 560. The controller 1910 may include hardware such as at least one processor or a microcomputer mounted on the main PCB 552, the auxiliary PCB 560, and other PCBs (e.g., light emitting device PCB 222). The controller 1910 may control an overall operation of each of the care tool sensor 290, proximity sensor 557, gyro sensor 558, sterilizer 220, memory 1920, and power supply device 1930 included in the main body 10.

The controller 1910 may receive a sensing value (e.g., a magnetic force measurement value or magnitude) from the care tool sensor 290. The controller 1910 may determine a type of care tool (e.g., first, second, or third care tools 70, 80, or 90) mounted on the head 20 of the main body 10 based on the received magnetic force measurement value. The controller 1910 may control the sterilizer 220 to turn on or off at least some of the plurality of light emitting devices 223 included in the sterilizer 220 based on the determined type of care tool. The controller 1910 may further determine whether an on condition of the sterilizer 220 is satisfied based on a sensing value received from at least one of the proximity sensor 557 and the gyro sensor 558. When the on condition is satisfied, the sterilizer 220 may be controlled to turn on the light emitting device 223. A control operation of the sterilizer 220 of the controller 1910 will be described in more detail with reference to FIGS. 20 to 23.

The memory 1920 may store various data necessary for the operation of the pet care device 1. The memory 1920 may collectively refer to a volatile memory and a nonvolatile memory provided in at least one of the main PCB 552, the auxiliary PCB 560, and other PCBs.

The memory 1920 may store sensing range information (i.e., magnetic force measurement value or magnitude range information) for each of the care tools 70, 80, and 90 that may be mounted on the head 20. When the magnetic force measurement value is received from the care tool sensor 290, the controller 1910 may determine the care tool mounted on the head 20 based on the magnetic force measurement value range information stored in the memory 1920.

The memory 1920 may store light emitting device control information for each of the care tools 70, 80, and 90. The light emitting device control information may include information about certain light emitting devices among the plurality of light emitting devices 223 that are turned on when a specific care tool is mounted, and information about light emission intensity or brightness of the light emitting devices that are turned on. When the type of mounted care tool is detected, the controller 1910 may control the sterilizer 220 based on the light emitting device control information corresponding to the detected care tool.

The light emitting device PCB 222 of the sterilizer 220 may be provided with a processor or a microcomputer that controls the plurality of light emitting devices 223 to turn on or off. The controller 1910 may transmit a control signal corresponding to the sensed care tool to the processor or the microcomputer of the sterilizer 220. The processor or the microcomputer of the sterilizer 220 may turn on or off at least some of the plurality of light emitting devices 223 in response to the received control signal. When the processor or the microcomputer is not provided in the light emitting device PCB 222, the controller 1910 may directly control at least some of the plurality of light emitting devices 223 to be on or off.

The power supply device 1930 may supply power required to operate each component or device (e.g., sterilizer 220, proximity sensor 557, gyro sensor 568, care tool sensor 290, controller 1910, and memory 1920) of the main body 10. The power supply device 1930 may include the battery 540 and the charging PCB 565 described above with reference to FIG. 7. The controller 1910 may control the power supply device 1930 to supply power to the sterilizer 220 when a specific care tool is mounted to turn on at least some of the light emitting devices 223. The power supply device 1930 may continuously supply a predetermined power or current to the sterilizer 220 even when the light emitting devices 223 are not turned on. A current value or magnitude of the power supplied to 220 may be increased to turn on at least some of the light emitting devices 223.

The main body 10 may include an output unit or user interface for outputting operation information or status information of a pet care device. The output unit may include at least one of a light 1940 and a speaker 1950. The light 1940 and the speaker 1950 may, as an example, be provided in the handle 50. Alternatively or in addition thereto, the light 1940 may be the red LED provided in the head 20 on the light emitting device PCB 220.

The light 1940 may include at least one LED that notifies the user of operation information or status information of the pet care device through a color or blinking method. The speaker 1950 may inform the user of operation information or status information of the pet care device via a sound or alarm. When the type of the care tool mounted on the head 20 is detected, the controller 1910 may provide information about the type of the detected care tool to the light 1940 and/or the speaker 1950, and the light 1940 and/or the speaker 1950 may produce a light or a sound, respectively, corresponding to the detected care tool. When the controller determines that the head 20 is detached from any of the care tools, the controller 1910 may turn off the light emitting devices 223 by turning off the power supply to the sterilizer 220. The user may be notified that the sterilizer 220 has been turned off through the light 1940 and/or the speaker 1950.

Figure 20:
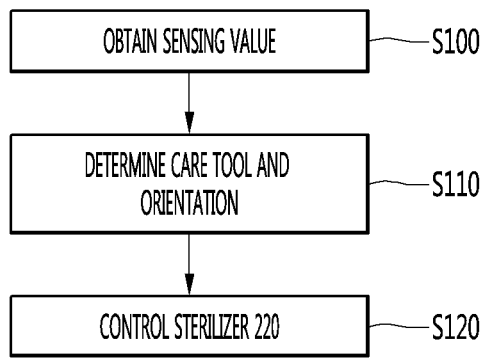
FIG. 20 is a flowchart for describing an embodiment in which the pet care device controls a sterilizer based on a care tool mounted in the main body.

Referring to FIG. 20, when the user turns power on via the operation switch 516, the care tool sensor 290 may sense a sensing value (e.g., magnetic force measurement value) from the care tool sensor 290 (S100). The controller 1910 may receive the sensed sensing value from the care tool sensor 290. The care tool sensor 290 may periodically obtain a sensing value and transmit the periodically obtained sensing value to the controller 1910. Alternatively, the care tool sensor 290 may only transmit the sensed sensing value to the controller 1910 when a change in sensed sensing values exceeds a predetermined change amount. The care tool sensor 290 may be implemented as a hall sensor that detects magnetism of a magnetic material such as a magnet. In this case, the sensing value may mean a magnetic force measurement value.

The controller 1920 may determine the care tool mounted on the head 20 based on the sensed sensing value (S110). The controller 1910 may determine a care tool mounted on the head 20 from the plurality of care tools 70, 80, and 90 based on the sensing value obtained from the care tool sensor 290. The controller 1910 may compare the sensed sensing value to a sensing value range designated to each type of care tool 70, 80, and 90 stored in the memory 1920. For example, the controller 1910 may receive a sensing value equal to or close to the first magnetic force. The controller 1910 may determine that the sensing value is within a first magnetic force range that incudes the first magnetic force and is stored in the memory 1920. In the memory 1920, the first magnetic force range may be data stored as first care tool sensing range information, and the controller 1910 may determine that the first care tool 70 is mounted. The controller 1910 may determine that a care tool is not mounted when a received sensing value is not included in the sensing value range information stored in the memory 1920 for each of the plurality of care tools 70, 80, and 90.

A state or orientation of the mounted care tool may further be determined based on the sensed sensing value. State or orientation information in the form of sensing value range information for each care tool 70, 80, or 90 may be stored in the memory 1920. As an example, the controller 1910 may detect that the second care tool 80 is incorrectly mounted to the head 20 (i.e., in a reversely mounted state) when the received sensing value is included in the state sensing value range included in the reverse orientation information stored in the memory 1920 for the second care tool 80. Step S110 includes not only detecting that the care tool is mounted on the head 20, but also detecting whether the care tool is mounted correctly or in reverse.

The pet care device may control the sterilizer 220 based on the sensed care tool (S120). The controller 1910 may control at least some of the plurality of light emitting devices 223 included in the sterilizer 220 to turn on according to the detected care tool. The sterilizer 220 may be controlled to be turned on or off and/or controlled to be at a certain intensity. The controller 1910 may control the sterilizer 220 based on the light emitting device control information of each of the care tools stored in the memory 1920.

For example, the light emitting device control information corresponding to the first care tool 70 may correspond to control information for turning on all of the light emitting devices 223 to a first intensity. The light emitting device control information corresponding to the second care tool 80 may correspond to control information for turning on only the light emitting devices 223 provided behind the light collecting surface 815 adjacent to the insertion portion 812. Control information for the second care tool 80 may also include control information for turning on the light emitting devices 223 to a second intensity. The first intensity and the second intensity may be the same or different. The light emitting device control information corresponding to the third care tool 90 may correspond to control information for turning off all of the plurality of light emitting devices 223.

The memory 1920 may further include light emitting device control information for a case when a care tool is not mounted. Even when a care tool is not mounted on the head 20, the pet care device 1 may be used to treat pet skin via a flat surface of the light diffuser 230, and light emitted from the light emitting device 223 through the light diffuser 230 may be irradiated to the skin of the pet. For example, the light emitting device control information for the case where a care tool is not mounted may correspond to control information for turning on at least some of the plurality of light emitting devices 223 to a third intensity. The third intensity may be lower than the first or second intensity, but is not necessarily so. As the sterilizer 220 is controlled, at least some of the plurality of light emitting devices 223 may be turned on or off, and the pet care device 1 may provide a skin care function according to the mounted care tool.

Figure 21:
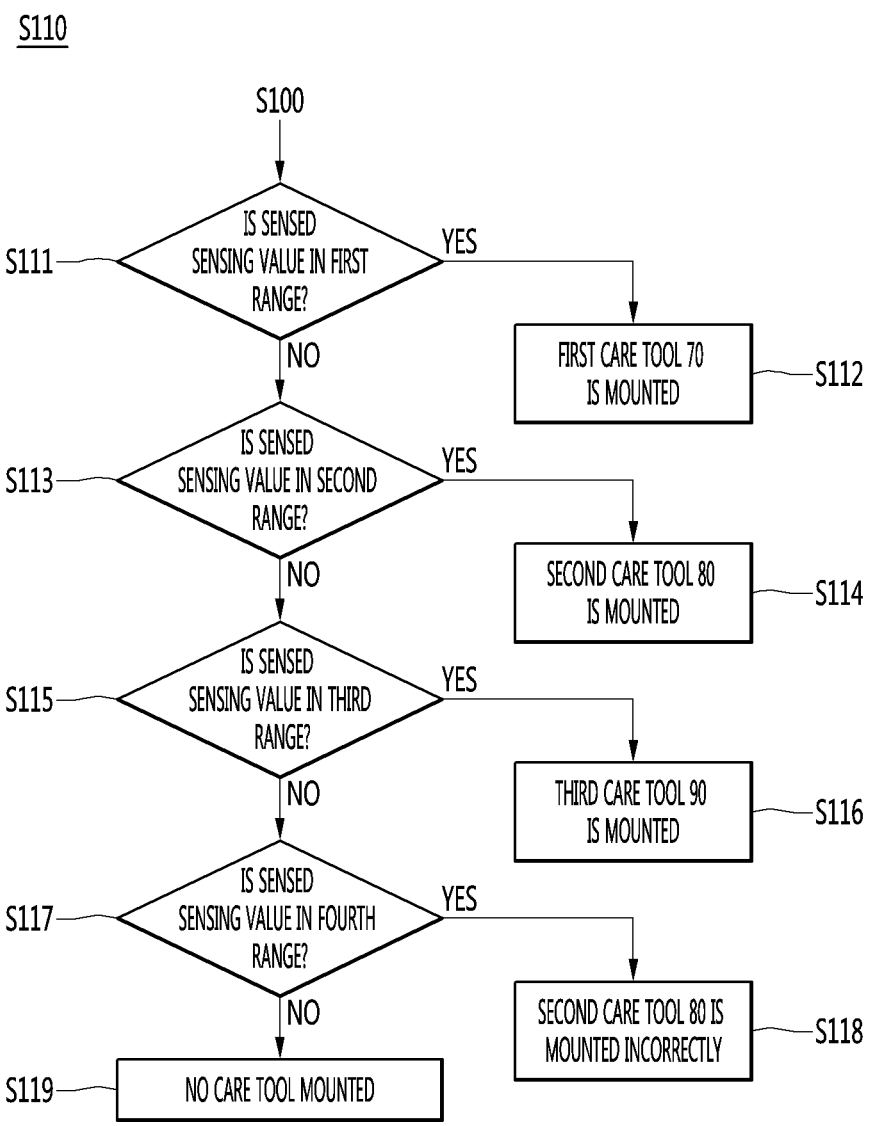
FIG. 21 is a flowchart for describing an embodiment of an operation in which a pet care device detects a care tool mounted on a main body.

Referring to FIG. 21, when a sensing value is obtained from the care tool sensor 290, the controller 1910 may detect the mounted care tool by comparing the obtained sensing value with a sensing value range corresponding to each of the care tools. Sensing value range information corresponding to each of the care tools may be stored in the memory 1920.

The memory 1920 may include a first range of sensing values corresponding to a proper mounting of the first care tool 70, a second range of sensing values corresponding to a proper mounting of the second care tool 80, and a third range of sensing values corresponding to a proper mounting of the third care tool 90. The memory 1920 may further include a fourth range of sensing values corresponding to a reverse or incorrect orientation or mounting of the first care tool 70, a fifth range of sensing values corresponding to a reverse or incorrect mounting or orientation of the second care tool 80, and a sixth range of sensing values corresponding to a reverse or incorrect mounting or orientation of the third care tool 90. When the controller senses sensing values in the fourth or sixth ranges, an operation may be the same as an operation when the controller senses sensing values in the first and third ranges, respectively, because the first and third care tools 70 and 90 are symmetrical. However, when the controller 1910 senses a sensing value in the fifth sensing range, the controller 1910 may sound the alarm 1940 or pulse the light 1930 to alert the user that the second care tool 80 is mounted in reverse or upside down. The controller 1910 may arbitrarily change a checking order of the first to sixth ranges, or may check the parallel to each of the first to sixth ranges.

The fourth and sixth ranges corresponding to the reverse orientations of the first and third care tools 70 and 90 may be included in the first and third ranges, respectively, and the fourth and sixth ranges may be omitted. As an alternative, the first and third care tools 70 and 90 may be symmetrical and may each include two magnets 722 and 922 at opposite sides of the first and third couples 720 and 920 such that, even if the first or third care tool 70 or 90 is mounted in reverse or upside down, the first or third magnetic forces may still be detected, respectively, and sensing values may still be within the first or third sensing value ranges, respectively. In this case, the memory 1920 may only store the fifth range of sensing values corresponding to a reverse or incorrect mounting of the second care tool 80, as the second care tool 80 may not operate properly unless the insertion portion 812 is aligned with light emitting devices 223 at an upper end of the head 20 that are controlled to turn on during an operation of the second care tool 80.

For convenience of description, in FIG. 21, a case where only incorrect mounting orientation for the second care tool 80 is stored in the memory 1920 will be described, while incorrect mounting orientation for the first and third care tools 70 and 90 are included in the first and third ranges, respectively. In such a case, the "fourth" range of sensing values may correspond to sensing values corresponding to a reverse or incorrect orientation of the second care tool 80.

When the received sensing value corresponds to the first range (YES in S111), the controller 1910 may determine that the mounted care tool is the first care tool 70 (S112). Based on the detection result, the controller 1910 may control the sterilizer 220 based on the light emitting device control information corresponding to the first care tool 70. For example, when the first care tool 70 is mounted, the sterilizer 220 may turn on the plurality of light emitting devices 223 to the first intensity. Alternatively or in addition thereto, the controller 1920 may turn on the ionizer 270.

When the received sensing value corresponds to the second range (YES in S113), the controller 1910 may detect that the mounted care tool is the second care tool 80 (S114). Based on the detection result, the controller 1910 may control the sterilizer 220 based on the light emitting device control information corresponding to the second care tool 80. For example, when the second care tool 80 is mounted, the sterilizer 220 may turn on only the light emitting devices 223 of the plurality of light emitting devices 223 adjacent to the insertion portion 812 and at a second intensity.

When the received sensing value corresponds to the third range (YES in S115), the controller 1910 may detect that the mounted care tool is the third care tool 90 (S116). Based on the detection result, the controller 1910 may control the sterilizer 220 based on the light emitting device control information corresponding to the third care tool 90. For example, when the third care tool 90 is mounted, the sterilizer 220 may not turn on the plurality of light emitting devices 223. The controller 1910 may also turn on the ionizer 270 when the third care tool 90 is mounted.

Meanwhile, referring to the drawings, the shapes of the head coupling portions 720, 820, and 920 of the inner body 210 and the care tools 70, 80, and 90 of the head 20 may be elliptical and vertically symmetric. Accordingly, each of the care tools 70, 80, and 90 may be mounted in a first direction or a second direction rotated 180° from the first direction. As shown in FIGS. 11 and 17, the plurality of teeth 714 of the first care tool 70 and the plurality of bristles 914 of the third care tool 90 are vertically symmetrical and left-right symmetrical. As an example, the first care tool 70 may be mounted to the head 20 such that the first connection portion 710c is located farther from the handle 50 than the second curved portion 710d, or alternatively such that the first curved portion 710c is located closer to the handle 50 than the second curved portion 710d. The same is true of the third care tool 90. Since the protrusion 714 and the brush 914 are symmetrical, the first care tool 70 and the third care tool 90 may be mounted in either the first direction or the second direction without loss in function.

The first care tool 70 may include two first fixing portions 724 such that one of the two fixing portions 724 is aligned with the care tool fixing portion 292 when the first care tool 70 is mounted in the first or second direction. The third care tool 90 may include two third fixing portions 924 such that one of the two third fixing portions 924 is aligned with the care tool fixing portion 292 when the second care tool 90 is mounted in the first or second direction. Alternatively or in addition thereto, the first care tool 70 may include two magnets 722, and one of the two magnets 722 may align with the care tool sensor 290 when the first care tool 70 is mounted in the first or second direction. The third care tool 90 may include two magnets 922, and one of the two magnets 922 may align with the care tool sensor 290 when the third care tool 90 is mounted in the first or second direction. In this alternative embodiment with two magnets 722 and 922 in each of the first and third care tools 70 and 90, sensed first and third magnetic forces may be the same regardless of a mounting orientation of the first and third care tools 70 and 90.

The first range corresponding to the first care tool 70 may include sensing values when the first care tool 70 is mounted in the first direction and when the first care tool 70 is mounted in the second direction. The third range corresponding to the third care tool 90 may include sensing values when the third care tool 90 is mounted in the first direction and when the third care tool 90 is mounted in the second direction.

In the case of the second care tool 80, since the insertion portion 812 may be formed closer to the first end 810a than the second end 810b of the tool body 810, the second care tool 80 may only be operated when mounted in the first direction. Accordingly, the memory 1920 may store sensing value range information further including fourth range information corresponding to when the second care tool 80 is mounted in the second direction.

When the sensed sensing value corresponds to the fourth range (YES in S117), the controller 1910 may determine that the second care tool 80 is mounted in the second direction (S118). In this case, the controller 1910 may control the sterilizer 220 to turn off the light emitting devices 223 or to maintain an off state. The controller 1910 may notify the user that the second care tool 80 is not properly mounted through the light 1940 and/or the speaker 1950.

As an alternative, the first range and the third range may have sensing range including only sensing values corresponding to when the care tools 70 and 90 are mounted in the first direction. In this case, when the care tools 70 and 90 are mounted in the second direction, a process similar to steps S117 and S118 may be performed for fifth and sixth ranges, respectively. The controller 1910 may notify the user of the incorrect mounting through at least one of the light 1940 and the speaker 1950.

If the received sensing value does not correspond to any values included in the first range to the fourth range (or the first range to the sixth range) (NO in S117), the controller 1910 may determine that a care tool is not mounted to the head 20 (S119). In this case, if the user has input an ON command via the command switch 516, the controller 1910 may determine that the user wants to use the pet care device 1 without a care tool mounted on the head 20. The controller 1910 may control the sterilizer 220 based on the light emitting device control information corresponding to the case where the care tool is not mounted. For example, when the care tool is not mounted, the sterilizer 220 may turn on the plurality of light emitting devices 223 to a third intensity.

The pet care device may accurately detect a type of care tool mounted on the head 20 using the care tool sensor 290 and control the light emitting devices 223 of the sterilizer 220 according to a pet care function provided by the detected care tool. The pet care device 1 may enable efficient driving of the sterilizer 220 by selectively controlling the light emitting devices 223 according to the sensed care tool. The pet care device may effectively provide various pet care functions with only one head 20 and a variety of swappable care tools 70, 80, and/or 90.

Figure 22:
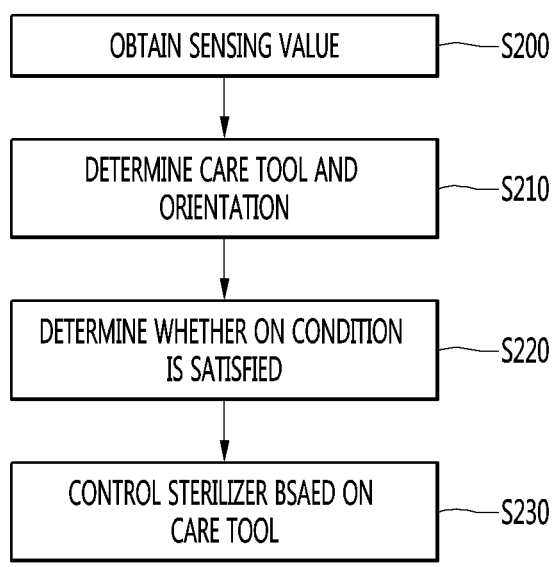
FIG. 22 is a flowchart for describing another embodiment of an operation in which the pet care device controls the sterilizer based on a care tool mounted to the main body.

Referring to FIG. 22, steps S200 and S210 are substantially the same as steps S100 and S110 described above with reference to FIG. 20, and a description thereof will be omitted. When the controller 1910 determines which, if any, care tool is attached to the head 20, the controller 1910 may determine whether an on condition of the sterilizer 220 is satisfied based on sensing information sensed by at least one of the proximity sensor 557 and the gyro sensor 558 (S220).

The proximity sensor 557 may detect whether the main body 10 (e.g., the head 20 or the handle 50) is close to (i.e., at the predetermined distance or less away from) the skin of the pet. The gyro sensor 558 may detect a vertical direction or orientation of the handle 50 to detect whether the care tool mounted on the head 20 and/or the light diffuser 230 faces downward and/or toward the skin of the pet. The on condition may be satisfied when the proximity sensor 557 detects that the main body 10 is the predetermined distance or less away from the pet skin or when the gyro sensor 558 detects that the light diffuser 230 is facing downward. Alternatively, the on condition may only be satisfied when both the proximity sensor 557 detects that the main body 10 is the predetermined distance or less away from the pet skin and when the gyro sensor 448 detects that the light diffuser 230 is facing downward.

When the controller 1910 determines in step S210 that the third care tool 90 is mounted or that the second care tool 80 is incorrectly mounted, the controller 1910 may not proceed to step S220.

When the on condition of the light emitting device 223 is satisfied in step S220, the pet care device may control the light emitting devices 223 of the sterilizer 220 based on the mounted care tool (S230).

The controller 1920 may receive periodic detection signals from the proximity sensor 557 and the gyro sensor 558. For example, the controller 1910 may determine that the on condition is no longer satisfied when the main body 10 is pulled away from the skin of the pet and the proximity sensor 557 senses that the main body 10 is at a distance greater than the predetermined distance away from the pet. The controller 1910 may also determine that the on condition is no longer satisfied when the light diffuser 230 is oriented upward based on a sensed orientation of the gyro sensor 558. When the controller 1910 determines that the on condition is no longer satisfied the controller 1910 may control the sterilizer 220 to turn off the light emitting devices 223.

The pet care device may turn on the light emitting devices 223 according to a skin care function of the care tool mounted to the head 20 to enable efficient power consumption. The pet care device may also operate the light emitting devices 223 based on a satisfaction of an on condition to prevent ultraviolet light of the light emitting devices 223 from being irradiated to an eyeball of the user and to reduce damaging side effects of ultraviolet light exposure.

Figure 23:
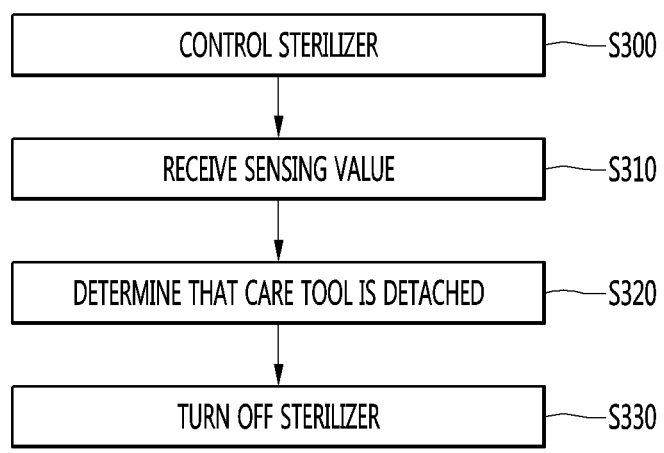
FIG. 23 is a flowchart illustrating an operation of detecting a detachment of a care tool and the head of the pet care device according to an embodiment.

Referring to FIG. 23, the pet care device may control the sterilizer 220 based on a sensed care tool mounted on the head 20 (S300). Step S300 is substantially the same as step S120 of FIG. 20, and a description thereof will be omitted.

The pet care device may receive periodic sensing values from the care tool 290 during the control of the sterilizer 220 (S310).

The care tool sensor 290 may periodically sense a sensing value even while performing the pet care function under the control of the sterilizer 220. The care tool sensor 290 may periodically transmit each of the sensed sensing values to the controller 1910, or may transmit the sensed sensing values when the sensed sensing values change by more than a predetermined change amount to the controller 1910.

The controller 1910 may determine a separation or detachment of a care tool based on the sensed sensing value (S320). As described above, each of the care tools 70, 80, and 90 may be mounted and fixed to the head 20 via first, second, and third magnetic forces between the care tool fixing portion 292 and the first, second, and third fixing portions 724, 824, and 924, respectively, which each include a magnet or a metal. When an external force of more than the first, second, or third magnetic force is applied to the first, second, or third care tool 70, 80, or 90, the first, second, or third care tools 70, 80, and 90 may be pulled and separated from the head 20.

The controller 1910 may detect that the care tool 70, 80, or 90 is separated when the sensed sensing value is not included in the first, second, third, fourth, (or fifth or sixth) sensing value ranges of the care tool mounted on the head 20. A separation of the care tool 70, 80, or 90 may include not only the case in which the care tool 70, 80, or 90 is completely separated from the head 20, but also the case in which the care tool is 70, 80 or 90 is partially separated by a predetermined displacement or more. The pet care device may control the sterilizer 220 to turn off the light emitting devices 223 when a separation of the care tool 70, 80, or 90 is detected (S330).

The controller 1910 may control the sterilizer 220 to turn off the light emitting devices 223 when a separation of the care tool 70, 80, or 90 is determined. For example, the sterilizer 220 may immediately turn off the light emitting devices 223 or alternatively may turn off the light emitting devices 223 by gradually decreasing brightness or intensity. According to an embodiment, when a separation of the care tool 70, 80, or 90 is detected, the controller 1910 may notify the user of the separation through at least one of the light 1940 and the speaker 1950.

When the third care tool 90 mounted on the head 20 is detached, the controller 1910 may simply maintain an off state of the light emitting devices 223 and inform the user that the third care tool 90 is detached via the light 1940 and/or the speaker 1950. Alternatively, when the third care tool 90 is mounted to the head 20, steps S310 to S330 may not be performed.

The pet care device may detect that the care tool 70, 80, or 90 mounted on the head 20 is separated by using the care tool sensor 290, and automatically turn off the light emitting device 223 based on the detection result. Accordingly, the care tool can be separated to prevent the pet care function from being performed inefficiently and to prevent waste of power.

Embodiments disclosed herein may be implemented as a pet care device that accurately detects a type of care tool mounted on a head by using a detection or care tool sensor provided in the head, and controls a light emitting device or sterilizer according to a pet care function provided by the detected care tool. Accordingly, the pet care device may enable efficient driving of the light emitting device by optimally controlling the light emitting device according to the sensed care tool. The pet care device may effectively provide various pet care functions with only one head.

When the pet care device performs a skin care function of the pet using a head or a care tool, the pet care device may recognize or determine satisfaction of an on condition of the light emitting device through a proximity sensor and a gyro sensor, and turn on the light emitting device, thereby enabling efficient power consumption of the light emitting device. Such a pet care device may be able to prevent ultraviolet light of the light emitting device from being irradiated to an eyeball of the user and to reduce side effects caused by such irradiation.

The pet care device may detect that the care tool mounted on the head is separated by using a detection or care tool sensor, and automatically turn off the light emitting device based on the detection result. Accordingly, the care tool may be separated to prevent the pet care function from being performed inefficiently and to prevent waste of power.

An object of the present disclosure is to provide a pet care device capable of sensing a type of care tool mounted on a head and controlling a plurality of light emitting devices according to the detected kind of care tool.

Another object of the present disclosure is to provide a pet care device that enables efficient power consumption of a plurality of light emitting devices provided in a head.

Embodiments disclosed herein may be implemented as a pet care device that identifies a care tool mounted on a head by using a sensor (e.g., Hall sensor) that acquires a sensing value related to a mounting of a care tool, and determines a light emitting device to operate based on the identified care tool. By controlling the plurality of light emitting devices included in a sterilizer, the sterilizer may be efficiently powered or driven. The pet care device may turn on or off at least one of the plurality of light emitting devices or adjust a light intensity based on the identified care tool.

The pet care device may detect sensing value range information including a sensing value from among sensing value range information corresponding to each of the plurality of care tools stored in a memory. The care tool mounted to the head may be identified.

Embodiments disclosed herein may provide a pet care device having a head provided with an inner body forming a space in which a head coupling portion of the care tool is mounted. The inner body and the head coupling portion may be symmetrical in a left-right or horizontal direction. The care tool may have a first direction and the head may be mounted in a second direction rotated 180° from the first direction.

When a light collecting surface formed on a tool body of the first care tool is symmetric among the plurality of care tools, the pet care device may be mounted with the first care tool in the first direction and the second direction, respectively. The light emitting device may be controlled by detecting an orientation.

When the light collecting surface formed on the tool body of a second care tool of the plurality of care tools is asymmetric, light may be collected when the pet care device detects that the second care tool is mounted in the first direction. The light emitting device of a first group corresponding to a surface may be turned on. If it is detected that the second care tool is mounted in a second direction, the pet care device turns off the plurality of light emitting devices or alternatively emits light of a second group symmetrical with the light emitting devices of the first group.

Embodiments disclosed herein may provide a pet care device that recognizes an on condition of a sterilizer based on a detection result of at least one of a proximity sensor and a gyro sensor, and controls the sterilizer to emit light when the on condition is recognized, thereby enabling efficient power consumption.

Embodiments disclosed herein may provide a pet care device that accurately detects a type of care tool mounted on the head by using a detection sensor or sensor provided in the head, and controls a sterilizer according to a pet care function provided by the detected care tool. Accordingly, the pet care device may enable efficient driving of the sterilizer by optimally controlling the sterilizer according to the sensed care tool, the pet care device can effectively provide various pet care functions with only one head.

When the pet care device performs a skin care function of the pet using a head or a care tool, the pet care device may recognize an on condition of the sterilizer through a proximity sensor and a gyro sensor and turn on the light sterilizer, thereby enabling efficient power consumption of the sterilizer. It may be possible to prevent ultraviolet light of the sterilizer from being irradiated to an eyeball of the user, and thereby prevent or reduce side effects.

The pet care device may detect that a care tool mounted on the head is separated by using a detection sensor, and automatically turn off the sterilizer based on the detection result. Accordingly, the care tool may be separated to prevent the pet care function from being performed inefficiently and to prevent waste of power.

The above description is merely illustrative of the technical idea of the present invention, and those skilled in the art to which the present invention pertains may make various modifications and changes without departing from the essential characteristics of the present invention.

The embodiments disclosed in the present invention are not intended to limit the technical idea of the present invention but to describe the present invention, and the scope of the technical idea of the present invention is not limited by these embodiments.

The protection scope of the present invention should be interpreted by the following claims, and all technical ideas within the equivalent scope should be interpreted as being included in the scope of the present invention.

As used herein, the term "ellipse" may be a concept that includes not only a geometric ellipse itself, but a form similar to an ellipse such as a geometric stadium (i.e., a rectangular having two semi-circles at opposite sides), a super ellipse, a lame curve, etc. An ellipse-like form may include a form including two straight lines and two curves connecting both sides of the two straight lines. Thus, "ellipse" as referred to in the specification means a concept that includes "ellipse itself and similar shapes to ellipses".

It will be understood that when an element or layer is referred to as being "on" another element or layer, the element or layer can be directly on another element or layer or intervening elements or layers. In contrast, when an element is referred to as being "directly on" another element or layer, there are no intervening elements or layers present. As used herein, the term "and/or" includes any and all combinations of one or more of the associated listed items.

It will be understood that, although the terms first, second, third, etc., may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section could be termed a second element, component, region, layer or section without departing from the teachings of the present invention.

Spatially relative terms, such as "lower", "upper" and the like, may be used herein for ease of description to describe the relationship of one element or feature to another element(s) or feature(s) as illustrated in the figures. It will be understood that the spatially relative terms are intended to encompass different orientations of the device in use or operation, in addition to the orientation depicted in the figures. For example, if the device in the figures is turned over, elements described as "lower" relative to other elements or features would then be oriented "upper" relative to the other elements or features. Thus, the exemplary term "lower" can encompass both an orientation of above and below. The device may be otherwise oriented (rotated 90 degrees or at other orientations) and the spatially relative descriptors used herein interpreted accordingly.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the disclosure are described herein with reference to cross-section illustrations that are schematic illustrations of idealized embodiments (and intermediate structures) of the disclosure. As such, variations from the shapes of the illustrations as a result, for example, of manufacturing techniques and/or tolerances, are to be expected. Thus, embodiments of the disclosure should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A hair and skin care device, comprising:
   a head on which a type of care tool among a plurality of types is mounted, the plurality of types including a first type;
   a plurality of light emitting devices provided in the head;
   a care tool sensor provided in the head and configured to sense a sensing value related to a mounting of the care tool; and a controller to determine a type of care tool mounted to the head and a direction the care tool is mounted based on the sensed sensing value and to control the light emitting device based on the determined type of care tool, wherein the first type of care tool includes a first light collecting surface, and the first type of care tool is not symmetrical across a horizontal axis and is arranged and positioned such that, when the first type is mounted in a first vertical direction, the first light collecting surface aligns with a first group of light emitting devices, and when the first type is mounted in a second vertical direction rotated 180° from the first vertical direction, the first light collecting surface aligns with a second group of light emitting devices different from the first group of light emitting devices, and wherein the controller controls the first or second groups of light emitting devices to turn on based on the determined type of care tool and whether the determined type of care tool is mounted in the first or second direction, and when the first type of care tool is mounted in the first vertical direction, the controller controls the first group of light emitting devices to turn on and the second group of light emitting devices to turn off.

2. The hair and skin care device of claim 1, further comprising a light emitting device printed circuit board (PCB), wherein the plurality of light emitting devices are spaced apart from each other on the light emitting device PCB, and the controller turns on or off at least one light emitting device among the plurality of light emitting devices based on the determined type of care tool.

3. The hair and skin care device of claim 2, wherein the plurality of types includes a second type of care tool which includes a second light collecting surface, and the controller turns on at least one light emitting device among the plurality of light emitting devices that is provided at a position corresponding to the first or second light collecting surface in the determined care tool.

4. The hair and skin care device of claim 2, wherein the controller is configured to adjust a light emission intensity of at least some of the light emitting devices among the plurality of light emitting devices based on the determined care tool.

5. The hair and skin care device of claim 1, further comprising a memory configured to store sensing value range information and light emitting device control information corresponding to different types of care tools, wherein the controller determines the type of care tool mounted by comparing the sensed sensing value to the sensing value range information stored in the memory, and controls the light emitting device based on light emitting device control information stored in the memory and corresponding to the determined care tool,
wherein the head has an inner body and the care tool has a head coupler, the inner body has a space in which the head coupler is inserted, and the inner body and the head coupler are symmetrical across a vertical axis.

6. The hair and skin care device of claim 5, wherein the second light collecting surface is symmetrical, and sensing value range information corresponding to the second type of care tool includes a first sensing value range corresponding to when the second type of care tool is mounted to the head in the first vertical direction a second sensing value range corresponding to when the second type of care tool is mounted to the head in the second vertical direction.

7. The hair and skin care device of claim 5, wherein the tool body of the first type of care tool is not symmetrical across a horizontal axis, sensing value range information corresponding to the first type of care tool includes a first sensing value range corresponding to when the first type of care tool is mounted to the head in the first vertical direction and a second sensing value range corresponding to when the first type of care tool is mounted to the head in the second vertical direction, the controller determines that the first type of care tool is mounted in the first vertical direction when the care tool sensor senses a sensing value in the first sensing value range, and the controller determines that the first type of care tool is mounted in the second vertical direction when the care tool sensor senses a sensing value in the second sensing value range.

8. The hair and skin care device of claim 1, wherein when the controller determines that the first type of care tool is mounted in the second vertical direction, all of the plurality of light emitting devices are turned off.

9. The hair and skin care device of claim 1, wherein, when the controller determines that the first type of care tool is mounted in the second vertical direction, the second group of light emitting devices is turned on, the first group of light emitting devices and the second group of light emitting devices being symmetrical across a horizontal axis.

10. The hair and skin care device of claim 1, wherein the controller determines whether the determined care tool is separated based on a sensing value sensed from the care tool sensor during control of the light emitting device, and when the controller determines that the determined care tool is separated, the light emitting device is turned off.

11. The hair and skin care device of claim 1, further comprising:
a proximity sensor to sense whether the head is a predetermined distance or less from an object to be treated; and
a gyro sensor to detect whether the head is directed to the object, wherein the controller determines whether an ON condition of the light emitting device is satisfied based on a detection result of at least one of the proximity sensor and the gyro sensor and turns on the light emitting device when the ON condition is satisfied.

12. The hair and skin care device of claim 1, wherein the care tool sensor is a hall sensor that senses a magnitude of a magnetic force.

13. A method of controlling a hair and skin care device, comprising:
sensing a sensing value related to a mounting of a care tool via a care tool sensor provided at a head;
identifying a type of care tool mounted to the head based on the sensed sensing value;
identifying an orientation of the type of care tool mounted on the head based on the sensed sensing value; and
controlling a plurality of light emitting devices provided in the head based on the identified care tool and the identified orientation, the plurality of light emitting devices including a first group of light emitting devices and a second group of light emitting devices, wherein, when, during identifying a type of care tool, a first type of care tool is identified, and when, during identifying an orientation of the type of care tool mounted, a first orientation is identified, controlling the plurality of light emitting devices includes controlling the first group of light emitting devices to be turned ON and the second group of light emitting devices to be turned OFF; and wherein, when the first type of care tool is identified and a second orientation is identified, controlling the plurality of light emitting devices includes controlling the first group of light emitting devices to be turned OFF.

14. The method of claim 13, wherein identifying the care tool mounted to the head includes:
   comparing sensing value range information corresponding to each of a plurality of types of care tools stored in a memory to the sensed sensing value;
   detecting a sensing value range that includes the sensed sensing value; and
   identifying the type of care tool corresponding to the detected sensing value range as the care tool mounted on the head.

15. The method of claim 13, wherein the identified care tool includes a light collecting surface, and when the first type of care tool is mounted in the first orientation, the first group of light emitting devices are provided at a position corresponding to the light collecting surface, and when the first type of care tool is mounted in the second orientation, the second group of light emitting devices are provided at a position corresponding to the light collecting surface of the identified care tool.

16. The method of claim 13, wherein controlling the plurality of light emitting device includes controlling a light emission intensity of at least one of the plurality of light emitting devices based on the identified care tool.

17. The method of claim 13, wherein controlling the plurality of light emitting devices includes:
   determining whether an ON condition of the light emitting devices is satisfied; and
   controlling at least one of the light emitting device to turn on when the ON condition is satisfied, wherein determining that the ON condition is satisfied includes at least one of determining that the head is a predetermined distance or less away from an object to be treated via a proximity sensor or determining that the head is facing the object to be treated via a gyro sensor.

18. The method of claim 13, further including determining whether the care tool is separated based on a sensing value sensed from the care tool sensor during control of the light emitting devices; wherein, when a separation of the care tool is determined, the light emitting devices are turned off.

19. A hair and skin care device, comprising:
   a head on which a care tool is mounted and removed from, the care tool being a first type, a second type, or a third type;
   at least one light emitting device provided in the head;
   a care tool sensor provided in the head and configured to sense a sensing value related to a mounting of the care tool; and
   a controller to determine a type of care tool mounted to the head based on the sensed sensing value and to control the light emitting device based on the determined type of care tool, wherein:
      the first type of care tool includes a plurality of bristles aligning with at least one first light collection surface such that light emitted from the light emitting device is transmitted through the plurality of bristles when the first type of care tool is mounted to the head;
      the second type of care tool includes an otoscope probe aligning with a second light collection surface such that light emitting from the light emitting device is transmitted through the otoscope probe; and
      the third type does not include a light collection surface such that light emitted from the light emitting device is not transmitted through the third type of care tool, wherein, when the controller determines that the third type of care tool is mounted to the head, the light emitting device is controlled to turn OFF.

20. The hair and skin care device of claim 19, wherein the light emitting device includes a plurality of light emitting devices, and the first light collection surface includes a plurality of light collection surfaces configured to align with the plurality of bristles, respectively, and wherein at least some of the plurality of light collection surfaces align with some of the light emitting devices when the first type of care tool is mounted to the head.

* * * * *